United States Patent [19]

Funakubo et al.

[11] Patent Number: 4,998,872
[45] Date of Patent: Mar. 12, 1991

[54] DENTAL CENTRIFUGAL CASTING APPARATUS

[75] Inventors: Tomoki Funakubo; Yasuharu Hakamatsuka; Mamoru Aihara; Kazuhiro Watanabe, all of Hachioji; Kiyozou Koshiishi; Sadao Shigetomi, both of Sagamihara, all of Japan

[73] Assignee: Olympus Optical Co., Ltd., Tokyo, Japan

[21] Appl. No.: 492,812

[22] Filed: Mar. 12, 1990

[30] Foreign Application Priority Data

Mar. 17, 1989 [JP] Japan .................................. 1-65569
Feb. 19, 1990 [JP] Japan .................................. 2-36316

[51] Int. Cl.⁵ .............................................. B29C 41/04
[52] U.S. Cl. ...................................... 425/143; 65/302; 164/150; 164/290; 425/425
[58] Field of Search .............. 164/150, 290, 335, 286, 164/287; 65/302; 425/425, 435, 143, 144

[56] References Cited

U.S. PATENT DOCUMENTS

| 4,156,452 | 5/1979 | Sharkey | 164/335 |
| 4,524,816 | 6/1985 | Plowman et al. | 164/287 |
| 4,524,817 | 6/1985 | Brugger et al. | 164/290 |
| 4,687,044 | 8/1987 | Wallace | 164/290 |
| 4,729,780 | 3/1988 | Shimuzu | 65/302 |

FOREIGN PATENT DOCUMENTS 60-166460 11/1985 Japan .
60-238073 11/1985 Japan .
62-77167 4/1987 Japan .
62-77168 4/1987 Japan .
2163684 3/1986 United Kingdom ................ 164/335

Primary Examiner—Willard E. Hoag
Attorney, Agent, or Firm—Frishauf, Holtz, Goodman & Woodward

[57] ABSTRACT

A dental centrifugal casting apparatus includes a crucible for receiving a dental casting material, a crucible holding unit for holding the crucible, a heating furnace such as a high-frequency induction heating furnace for heating and melting the dental casting material in the crucible, a crucible forward and backward rotary driving unit for driving the crucible holding unit forward and backward so as to insert the crucible into the heating furnace to heat and melt the material in the crucible and remove the crucible from the furnace, and for rotationally driving the crucible holding unit so as to inject the melted material into a mold at a predetermined position, a bucket for holding the mold in which the molten material is injected by the forward and backward motion and the rotation of the crucible performed by the crucible forward and backward rotary driving unit, and a centrifuge unit for rotating a rotary arm swingably mounting the bucket on its end portion at high speed immediately after the material is injected to apply a centrifugal force to the mold and molten material, thereby performing casting.

11 Claims, 16 Drawing Sheets

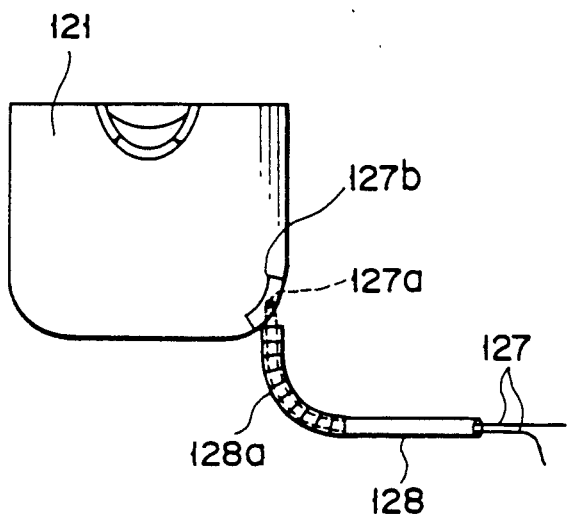
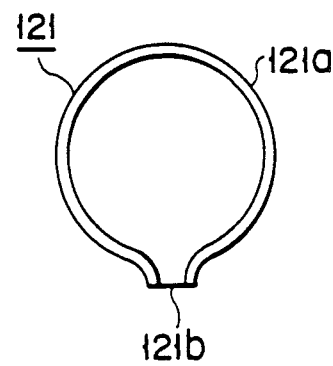
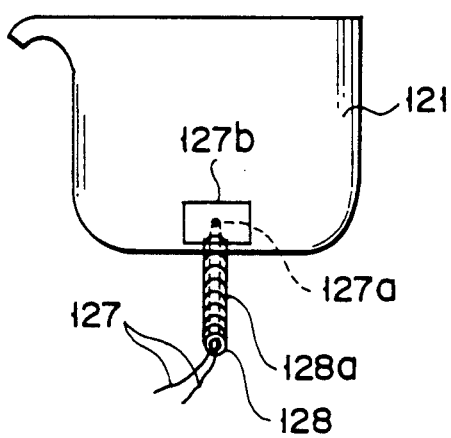
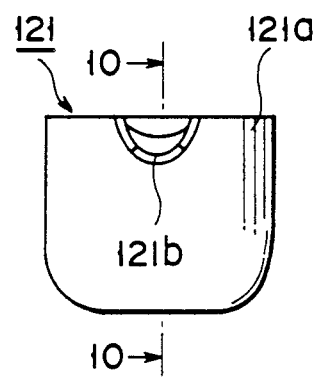
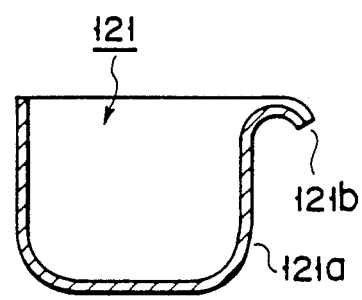
FIG. 6
FIG. 8
FIG. 7
FIG. 9
FIG. 10

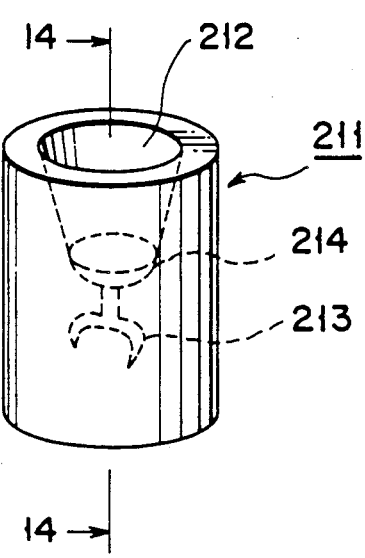
F I G. 13
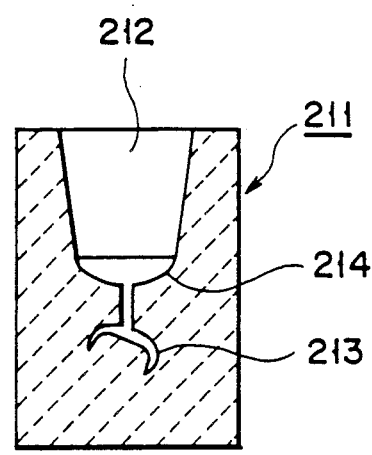
F I G. 14
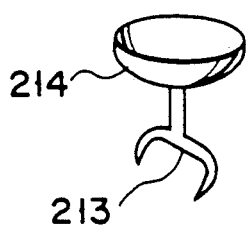
F I G. 15
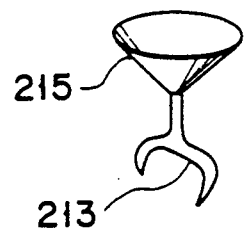
F I G. 16
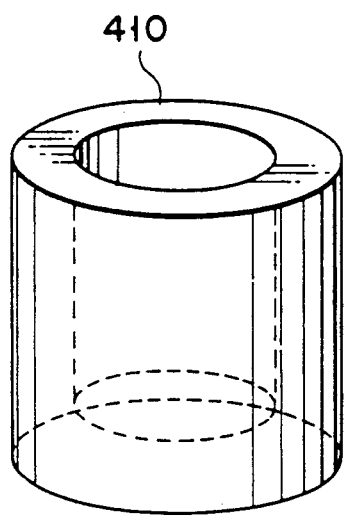
F I G. 17
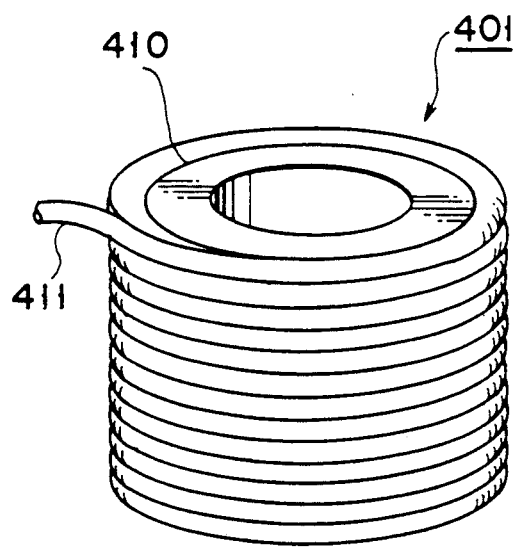
F I G. 18

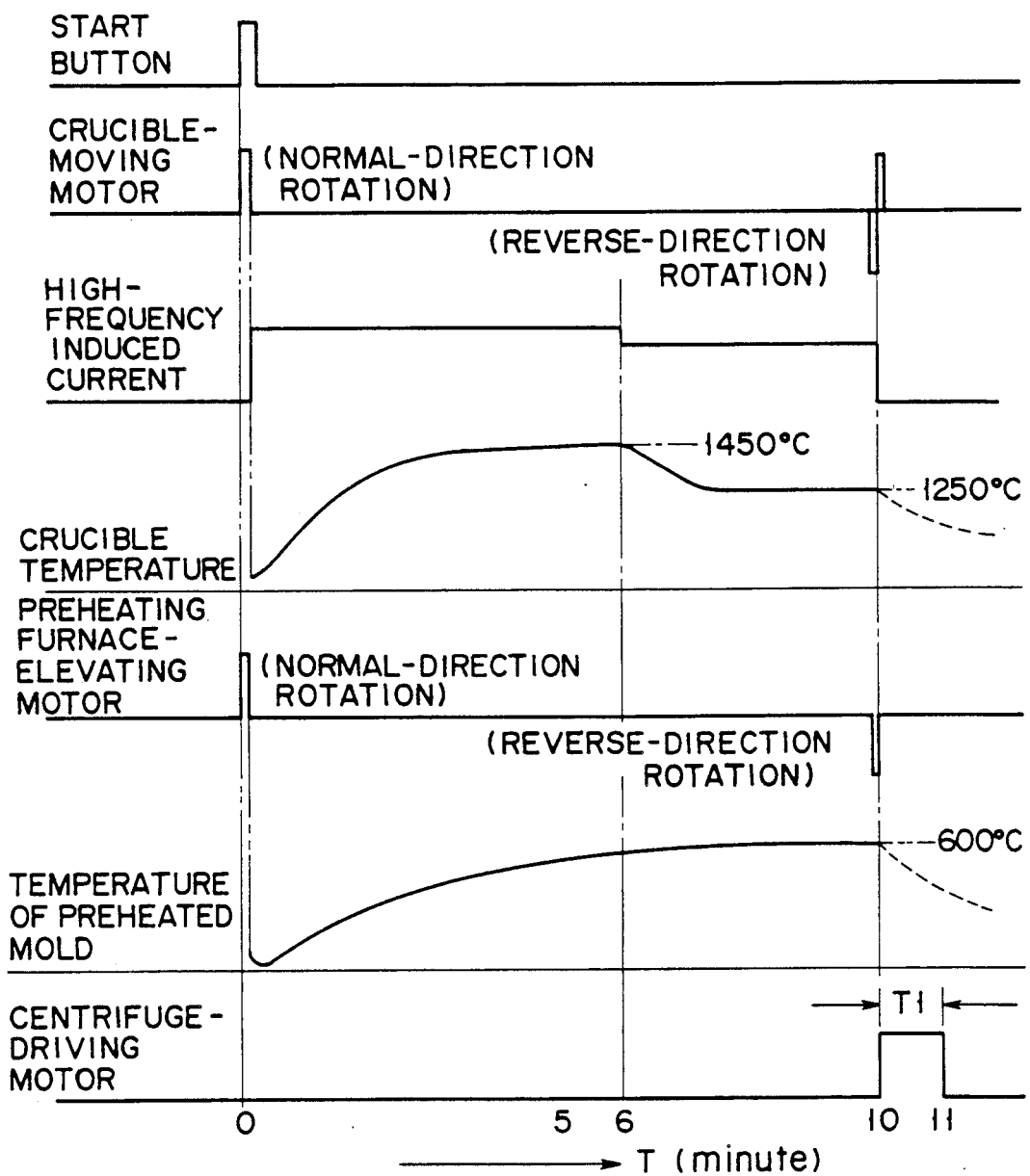
F I G. 21

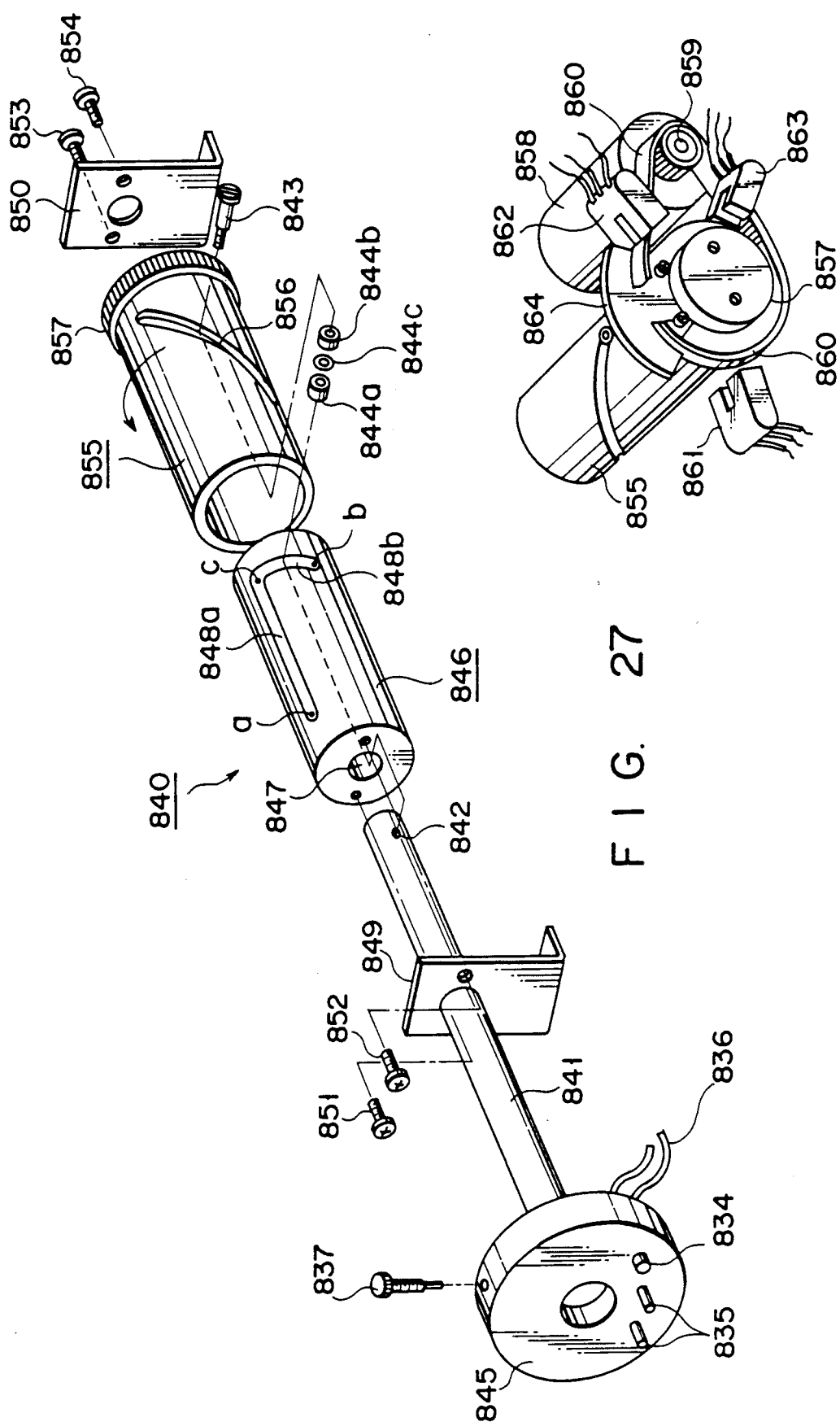

DENTAL CENTRIFUGAL CASTING APPARATUS

BACKGROUND OF THE INVENTION

1. Field of the Invention

The present invention relates to a dental centrifugal casting apparatus for casting an artificial tooth such as an artificial crown by using, e.g., glass ceramic as a casting material.

2. Description of the Related Art

Conventionally, metal materials such as a gold alloy and a nickel-chromium alloy have been used as a material for casting an artificial tooth such as an artificial crown. Melting temperatures of these metal materials fall within the range of 1,000° C. to 1,100° C., i.e., comparatively low. Therefore, a resistant-heating electric furnace has been used as a material heating/melting means for use in a conventional dental centrifugal casting apparatus. In order to cast an artificial tooth such as an artificial crown, the above material heated/melted in the electric furnace is flowed into an investment preheated at 400° C. to 500° C., and then a manual centrifuge is operated to perform centrifugal casting. That is, casting has been conventionally performed by such a simple manual operation.

In recent years, however, a glass ceramic material having good affinity to a living body is used as an artificial tooth material. A melting temperature of this glass ceramic material is about 1,300° C. to 1,500° C., i.e., much higher than that of the conventional metal materials. When a material having such a high melting temperature is used, cast products having uniform characteristics cannot be stably manufactured by the conventional manufacturing process since casting must be performed under strict casting conditions.

In order to solve this problem, various types of artificial tooth casting apparatuses improving the conventional manufacturing process have been proposed. For example, Published Unexamined Japanese Utility Model Application No. 60-166460 discloses an apparatus of this type. Such an apparatus, however, is generally large in size. In addition, a highly skilled operator is required to operate the apparatus of this type in order to cast a metal into an artificial tooth. That is this apparatus cannot be easily used for dental casting apparatus.

SUMMARY OF THE INVENTION

It is an object of the present invention to provide a dental centrifugal casting apparatus which allows an unskilled operator to easily perform casting, can finish casting before cooling/solidification of a casting material progress, can protect a material from being overflowed from a mold due to a shock upon start of rotation of a centrifuge or a centrifugal force during high-speed rotation, can easily obtain a cast product such as a high-quality artificial crown, and can heat/melt a casting material with high efficiency.

In order to achieve the above object, the present invention provides the following basic means.

That is, there is provided a dental centrifugal casting apparatus comprising a crucible for receiving a dental casting material, a crucible holding unit for holding the crucible, a heating furnace composed of, e.g., a high-frequency induction heating device and provided to heat/melt the dental casting material in the crucible, a crucible forward/backward rotary driving unit for driving forward/backward the crucible holding unit so as to insert/remove the crucible into/from the heating furnace to heat/melt the material in the crucible, and for rotationally driving the crucible holding unit so as to inject the heated/melted material into a mold at a predetermined position, a bucket for holding the mold in which the molten material is injected by the forward/backward motion and the rotation of the crucible performed by the crucible forward/backward rotary driving unit, and a centrifuge unit for rotating a rotary arm swingably mounting the bucket on its end portion at high speed immediately after the material is injected to apply a centrifugal force to the mold and molten material, thereby performing casting.

The above means provides the following effects.

(1) A series of processes such as heating/melting of a material, injection of the material into the mold, and rotation and stop of the centrifuge can be performed substantially automatically. Therefore, even an unskilled operator can easily operate the casting apparatus to perform casting.

(2) Since the centrifuge rotates at high speed at the same time the heated/melted material is injected in the mold, casting can be finished before cooling/solidification of the casting material progresses.

(3) Since the position of the mold changes in accordance with the rotation of the centrifuge unit, the molten material is protected from being overflown from the mold due to a shock upon start of rotation of the centrifuge unit or a centrifugal force during high speed rotation.

(4) A heating furnace such as a high-frequency induction heating device is used as a heating/melting means. Therefore, the casting material can be heated/melted with high efficiency, and the apparatus can be made compact.

It is another object of the present invention to provide a dental centrifugal casting apparatus for facilitating practically smooth use, the apparatus, including measuring means for correctly measuring a crucible temperature means for preventing, e.g., a furnace member, a crucible holding member and a coupling flange from being adversely thermally affected, means for easily replacing a crucible holding unit at an arbitrary timing, and means for rapidly and correctly driving the crucible holding unit forward/backward and rotationally.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 1 to 21 show the first embodiment of the present invention, in which:

FIG. 1 is a front view showing an installation state of a dental centrifugal casting apparatus;

FIG. 2 is a sectional view taken along a line 2—2 of FIG. 1;

FIG. 3 is a plan view showing a casting material melting portion of a casting apparatus main body;

FIGS. 4 and 5 are views showing a crucible holding unit in detail;

FIGS. 6 and 7 are views showing a platinum-based thermocouple;

FIGS. 8 to 10 are views showing the shape of a crucible;

FIG. 11 is a view showing a state of a bucket mounted in a bucket holder and a positional relationship between the movement of the bucket and base plates for partitioning a box member;

FIG. 12 is a perspective view showing an outer appearance of the bucket;

FIG. 13 is a perspective view showing a detailed structure of a mold to be held in the bucket;

FIG. 14 is a sectional view taken along a line 14—14 of FIG. 13;

FIGS. 15 and 16 are perspective views schematically showing a bottom structure of a molten material receiving portion of the mold;

FIGS. 17 and 18 are perspective views showing an arrangement of a mold-preheating furnace;

FIG. 19 is a plan view showing a positional relationship between a centrifugal casting portion, a rotary driving portion and a mold preheating portion;

FIG. 21 is a timing chart showing a series of operations of the casting apparatus; and FIGS. 22 to 29 are views showing the second embodiment of the present invention, in which:

FIG. 22 is a front view showing an installation state of a dental centrifugal casting apparatus;

FIG. 23 is a side view showing the interior of a casting apparatus main body;

FIG. 24 is a plan view showing the interior of the casting apparatus main body;

FIG. 25 is a side view showing a crucible holding unit;

FIG. 26 is a plan view showing a crucible held in the crucible holding unit;

FIGS. 27 and 28 are exploded perspective views showing an arrangement of a crucible forward/backward rotary driving unit; and FIG. 29 is a perspective view showing only a main part of the casting apparatus main body by omitting a part thereof.

DETAILED DESCRIPTION OF THE PREFERRED EMBODIMENTS

(1st Embodiment)

Figure 1:
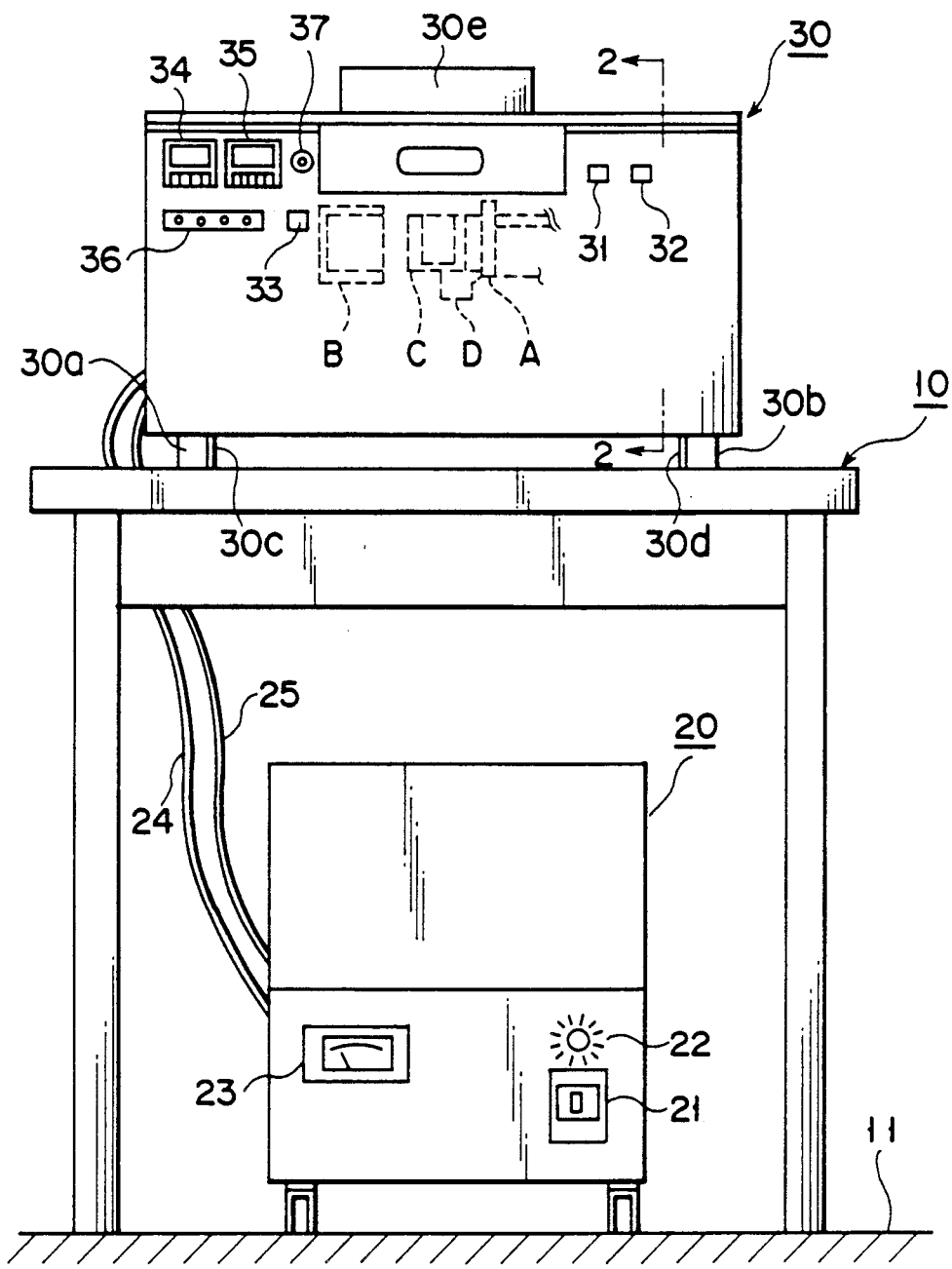

FIG. 1 is a front view showing an installation state of a dental centrifugal casting apparatus according to the first embodiment of the present invention. Referring to FIG. 1, reference numeral 10 denotes a casting apparatus installation table. A power supply/control unit 20, a cooling unit (not shown) and the like are placed on a floor 11 below the table 10. A casting apparatus main body 30 is placed on the table 10.

Although not shown, the power supply/control unit 20 includes a high-frequency power supply, a sequence control circuit and the like. A main switch 21, an ON/OFF indication lamp 22, an ammeter 23 and the like are arranged on a front surface of a box member of the unit 20. Note that the main switch 21 has a circuit breaker function.

A high-frequency power cable 24 for supplying high-frequency power to the casting apparatus main body 30 and a control signal cable 25 for supplying a control signal to the main body 30 are extracted from the power supply/control unit 20. The other end of each of the cables 24 and 25 is connected to the casting apparatus main body 30. Therefore, when the main switch 21 is turned on, the ON/OFF indication lamp 22 is turned on, and the main body 30 is set in a standby state before a main operation. The ammeter 23 indicates a value of a high-frequency current to be supplied to the main body 30.

The casting apparatus main body 30 has four legs 30a to 30d on its box member bottom surface. The length of at least three out of the four legs can be adjusted. By adjusting the lengths of these legs, therefore, the main body 30 can be horizontally placed on the table 10. A chimney 30e for exhausting heat generated by a high-frequency induction heating furnace (to be described later) outside the casting apparatus main body 30 is provided on the upper surface of the box member of the main body 30.

A start button 31, a reset button 32, a stop button 33, a crucible temperature indicator 34, a mold-preheating furnace temperature indicator 35, progression lamps 36, an alarm lamp 37 and the like are arranged on a panel on the front surface of the box member of the main body 30.

The start button 31 is used to supply a command to a sequence control circuit included in the power supply/control unit 20 to start a sequential operation. The stop button 33 is used to simultaneously stop all the operations including the sequence of the overall apparatus. The crucible temperature indicator 34 is used to receive a signal from a thermocouple mounted on a material melting crucible (to be described later) to indicate the temperature of the crucible. The mold-preheating furnace temperature indicator 35 is used to receive a signal from a thermocouple placed in a mold-preheating furnace (to be described later) to indicate the temperature of the mold-preheating furnace. The progression lamps 36 are used to indicate a progression state of a casting operation and sequentially turned on one after another in accordance with the progression state of the operation sequence in the casting apparatus main body 30. The alarm lamp 37 is turned on when an abnormal phenomenon as described in the following item (1) or (2) occurs while the casting apparatus main body 30 is in operation.

(1) An amount of water flowing through a work coil becomes smaller than a predetermined amount.

(2) An excessive current flows through a high-frequency power supply circuit.

When the alarm lamp 37 is turned on, the operation of the overall apparatus is stopped. When an operation is stopped by the stop button 33 or when the alarm lamp 37 is turned on to stop an operation, the reset button 32 is used to execute an operation for returning the crucible or the mold-preheating furnace from the stop position to its initial position.

Various constituting parts (to be described later) are included in the casting apparatus main body 30. One feature of this embodiment is that a material of a coupling flange indicated by a broken line portion A in FIG. 1, a material of a furnace member indicated by a broken line portion B therein, a material of a crucible holding member indicated by a broken line portion C therein, a crucible temperature measuring means indicated by a broken line portion D therein and the like are specified.

In order to clarify the above feature and a detailed structure of each part, an internal arrangement of the casting apparatus main body 30 will be described below.

Figure 2:
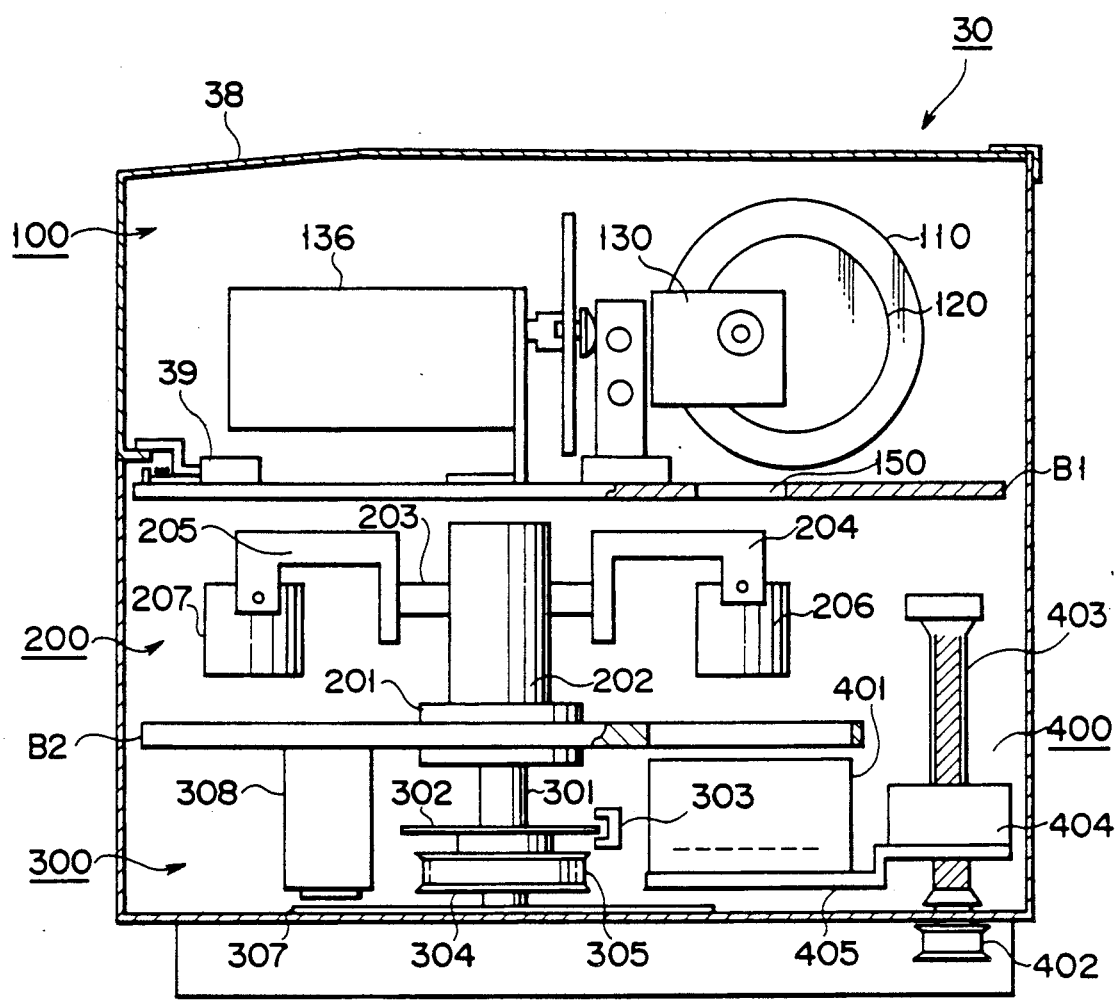

FIG. 2 is a sectional view taken along a line 2—2 in FIG. 1. As shown in FIG. 2, the interior of the casting apparatus main body 30 is partitioned by two base plates B1 and B2 to form a 3-stage structure with upper, middle and lower stages. The upper stage serves as a casting material melting section 100 for heating/melting a casting material. The middle stage serves as a centrifugal casting section 200 for rotating a mold containing a molten material to mold the molten material in the mold by using a centrifugal force. The lower stage serves as a rotary driving section 300 for rotationally driving the centrifugal casting section 200 and a mold preheating section 400 for preheating a mold before a molten material is injected in the mold.

The casting material melting section 100 shown in the upper stage in FIG. 2 comprises a high-frequency induction heating furnace 110, a crucible holding unit 120, and a crucible forward/backward rotary driving unit 130 as will be described later. Reference numeral 136 denotes a driving motor for the unit 130.

The centrifugal casting section 200 shown in the middle stage in FIG. 2 comprises a bearing 201, a rotary shaft 202 rotatably supported by the bearing 201, a rotary arm 203 supported by the rotary shaft 202, bucket holders 204 and 205 mounted on two ends of the rotary arm 203, a first bucket 206 swingably held at the distal end of the bucket holder 204, and a second bucket 207 swingably held at the distal end of the bucket holder 205.

The rotary driving section 300 shown in the lower stage in FIG. 2 comprises a shaft member 301 for rotationally driving the rotary shaft 202 of the centrifugal casting section 200, a slit plate 302 fitted in the shaft member 301 and having slits (not shown) formed in part thereof, a photosensor 303 having a light-emitting portion and a light-receiving portion sandwiching the slit formation portion of the slit plate 302 in a non-contact state, a pulley 304 fitted on the shaft member 301, a motor 306 (not shown in FIG. 2) for applying power to the pulley 304 via a belt 305, a disc 307 which consists of a ferromagnetic substance and rotates together with the shaft member 301, and an electromagnetic chuck 308 which is arranged close to one surface of the disc 307 and attracts the disc 307 as needed to stop free rotation of the shaft member 301 and therefore free rotation of the overall rotary section including, e.g., the centrifugal casting section 200, thereby positioning the first and second buckets 206 and 207.

Note that the slits of the slit plate 302 are formed in a position corresponding to an angular position of the bucket 206 (207). The electromagnetic chuck 308 operates in accordance with a control signal from the power supply/control unit 20.

The mold preheating section 400 shown in the lower stage in FIG. 2 comprises a mold-preheating furnace 401, a pulley 402 to be rotationally driven by a preheating furnace-elevating motor 406 (not shown in FIG. 2), a change nut 403 which rotates together with the pulley 402, a nut receiver 404 which meshes with a threaded portion of the change nut 403 and vertically moves upon rotation of the nut 403, and a support member 405 having a proximal end portion mounted on the nut receiver 404 and a distal end portion for supporting the mold-preheating furnace 401.

During an operation period of the casting apparatus main body 30, an upper cover 38 is locked so as not to be opened by a lock solenoid 39. Even if the upper cover 38 is open during the operation period, a high-frequency current supplied to the casting material melting section 100 is cut off by a door interlock switch (not shown), and the operations of the centrifugal casting section 200 and the like are stopped.

Figure 3:
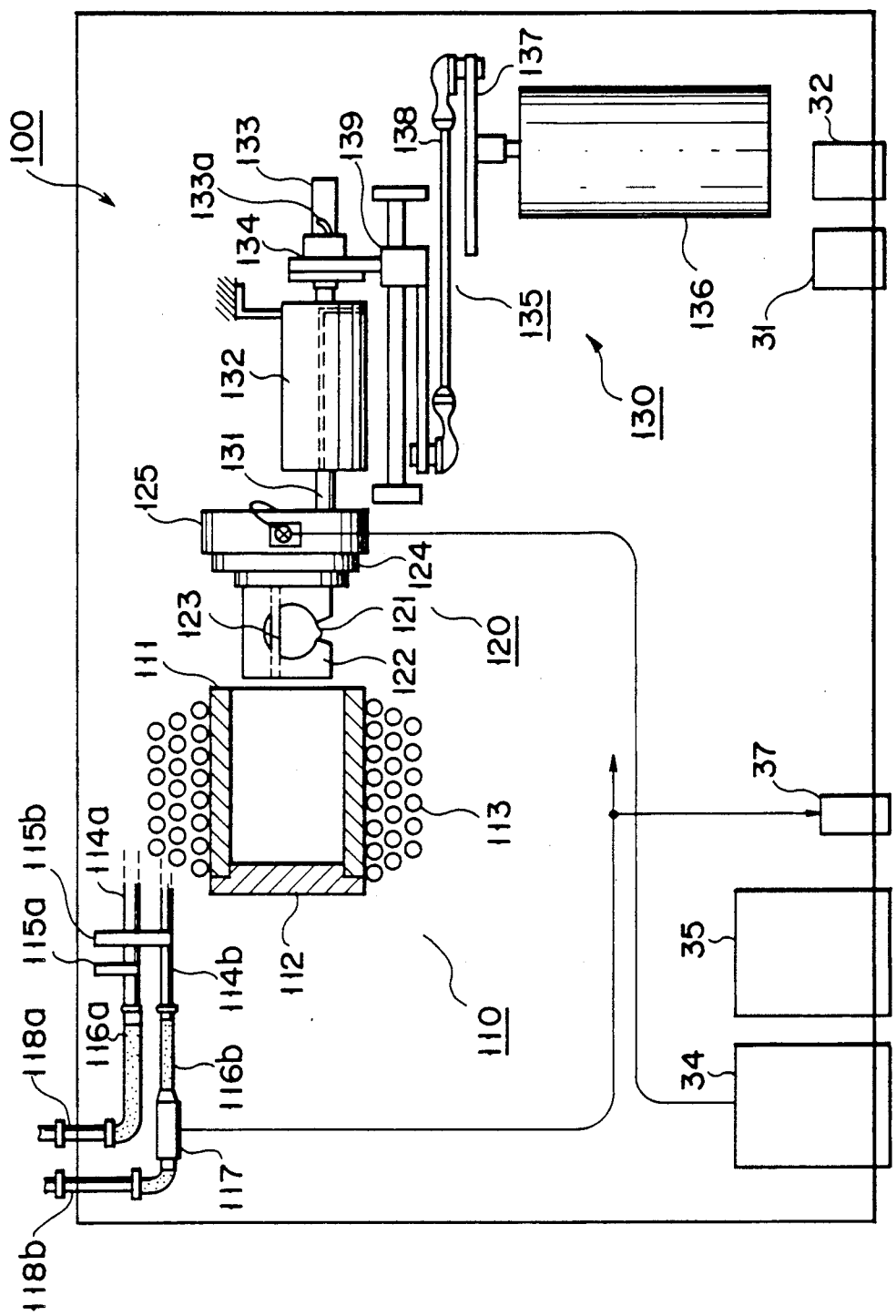

FIG. 3 is a plan view showing an arrangement of the casting material melting section 100 of the casting apparatus main body 30 shown in FIG. 2. As shown in FIG. 3, the section 100 is constituted by the high-frequency induction heating furnace 110, the crucible holding unit 120 and the crucible forward/backward rotary driving unit 130.

The high-frequency induction heating furnace 110 comprises a heat-insulating cylinder 111, a bottom wall heat-insulating plate 112 which consists of the same material as the cylinder 111 and closes one open end (at the left side in FIG. 3), a work coil 113 made of, e.g., a copper pipe wound around the outer circumferential surface of the cylinder 111 and covered with an insulating coating, and pipes 114a and 114b for circulating cooling water between the work coil 113 and a cooling unit (not shown) and supplying a high-frequency current from the power supply/control unit 20 to the work coil 113.

The heat-insulating cylinder 111 and the bottom wall heat-insulating plate 112 are made of an alumina fiber board having a high thermal shock resistance and a high heat resistance. The alumina fiber board is obtained by mixing a filler and an organic or inorganic binder in a fiber material mainly consisting of an alumina fiber and forming the resultant material into a board. Examples of the material is "RF BOARD 17HD" and "RF BOARD 18HD" (tradenames) available from NICHIAS CORP and "FIBER MAX 16-R BOARD" and "FIBER MAX 17-D BOARD" (tradenames) available from Toshiba Monoflux Co., Ltd.

When a casting material is melted in the crucible of the high-frequency induction heating furnace 110, the other open end (at the right side in FIG. 3) of the heat-insulating cylinder 111 is closed by a cover member heat-insulating plate 124 (to be described later) consisting of the same material as the heat-insulating plate 112. As a result, the interior and exterior of the furnace 110 are thermally insulated.

Terminals 115a and 115b are mounted on the pipes 114a and 114b, respectively. A high-frequency current of about 27 kHz and several tens to several hundreds mA is supplied from the power supply/control unit 20 to the terminals 115a and 115b. In this manner, the work coil 113 is powered via the pipes 114a and 114b. As shown in FIG. 3, in order to electrically insulate the work coil 113 from the cooling unit, an insulating Tetron hoses 116a and 116b are inserted between the pipes 114a and 114b and water supply and drainage ports 118a and 118b at the cooling unit side, respectively. A flow amount switch 117 is mounted on the hose 116b. When a cooling water flow rate becomes lower than a predetermined level, the switch 117 outputs an ON (or OFF) signal to turn on the alarm lamp 37 and to step the sequence in the casting apparatus main body 30. As a result, abnormal overheating of the work coil 113 due to an insufficient cooling water flow rate can be prevented.

The crucible holding unit 120 comprises a platinum based crucible (to be referred to as a "platinum crucible" hereinafter) 121, a crucible holding member 122 for stably holding the platinum crucible 121, a platinum pin 123 for pressing the crucible, a cover member heat-insulating plate 124 for closing the other open end of the heat-insulating cylinder 111, and a coupling flange 125 for coupling the crucible holding member 122 to an operation shaft 131 of the crucible forward/backward rotary driving unit 130 to satisfy a predetermined positional relationship.

Figure 4:
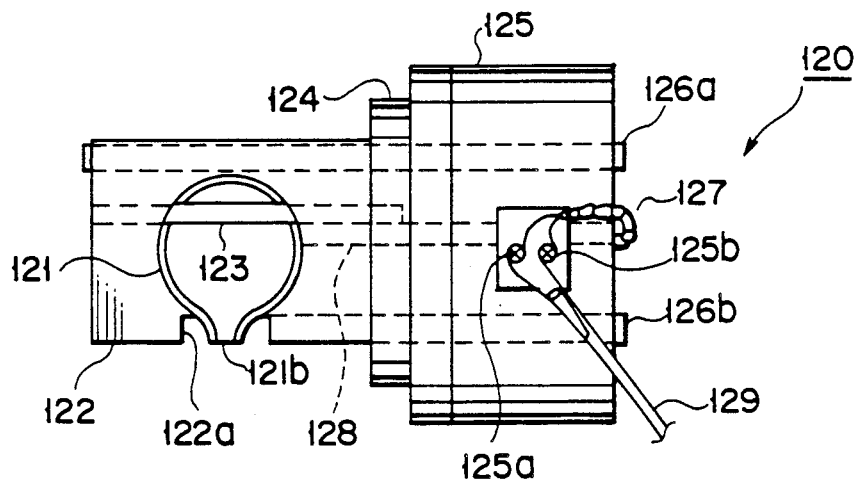
Figure 5:
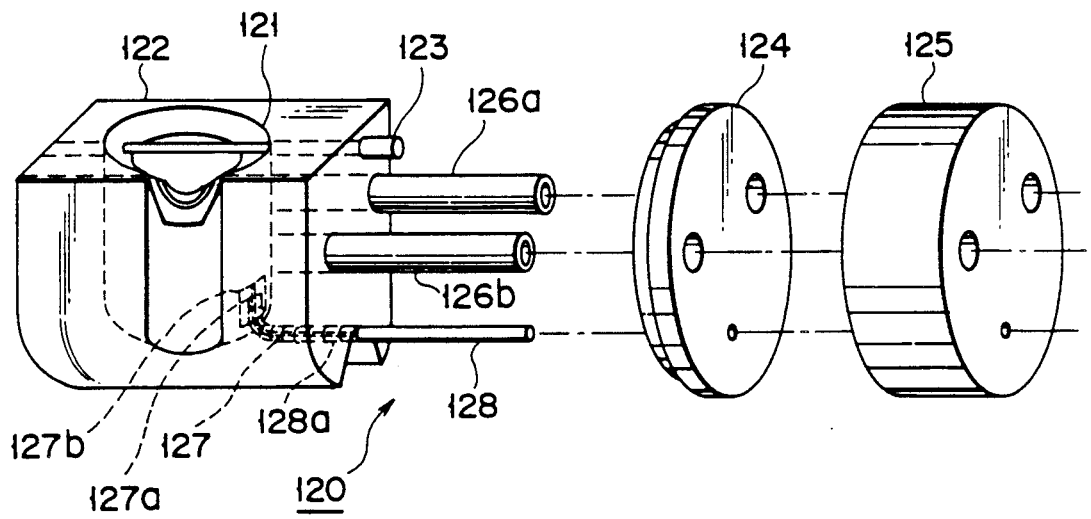

FIGS. 4 and 5 are views showing the crucible holding unit 120 in detail. As shown in FIGS. 4 and 5, a recess having substantially the same dimensions as the outer dimensions of the crucible 121 is formed in the crucible holding member 122 to stably hold the crucible 121. Note that when the crucible holding member 122 is tilted upon injection of a molten material, the crucible 121 may be dropped from the member 122. Therefore, the locking platinum pin 123 is inserted in the member 122. That is, the pin 123 presses an opening portion of the crucible 123 from outside (above).

The crucible holding member 122 consists of an alumina fiber board similar to the heat-insulating cylinder 111, the bottom wall heat-insulating plate 112, and the cover member heat-insulating plate 124. As shown in FIG. 4, a recessed notched portion 122a is formed in a portion of the crucible holding member 122 immediately below a crucible molten material injection port. When a molten material such as a glass material in the crucible 121 is injected into a mold (to be described later), this notched portion prevents the molten material from being adhered or stacked on the portion of the member 122 immediately below the molten material injection port. One end of each of alumina pipes 126a and 126b as support members is inserted in the crucible holding member 122. The other end of each of the pipes 126a and 126b projecting from the member 122 extends through the cover member heat-insulating plate 124 made of a alumina fiber board consisting of the same material as the button wall heat-insulating plate 112. The end portions of the pipes 126a and 126b are inserted in a coupling flange 125 and fixed by machine screws (not shown).

As shown in FIGS. 6 and 7, a scald contact portion 127a of a platinum-based thermocouple (R-Type) 127, which is covered with a platinum piece 127b, is connected to the outer surface of the platinum crucible 121 by means of, e.g., "scalding" at a comparatively low temperature. Both the end portions of the thermocouple 127 are extracted outside the crucible holding unit 120 through the inside of an alumina protecting ring 128a and through an alumina protecting tube extending through the cover member heat-insulating plate 124 and the coupling flange 125.

Referring back to FIG. 4, both the end portions of the thermocouple 127 extracted outside the unit 120 through the inside of the tube 128 are fixed on the outer circumferential surface of the flange 125 together with two end portions at one end of extension lead wires 129 of the thermocouple 127, respectively, by machine screws. Two end portions at the other end of the wire 129 are guided to and connected to the crucible temperature indicator 34 described above.

The crucible temperature measuring means provided as described above can obtain correct temperature information following only a heating temperature of the crucible 121 without being adversely affected by electromagnetic induction caused by an induction heating means. In addition, both the end portions of the thermocouple 127 are fixed on the outer circumferential surface of the coupling flange 125 as a part of the crucible holding unit 120 and then connected to the extension lead wire 129 of the thermocouple 127. Therefore, even when the unit 120 rotates about the operation shaft 131, a bending or twisting stress produced by the rotation does not act on the thermocouple 127. Therefore, the crucible heating temperature can be constantly, stably and correctly measured, and correct temperature control based on the measurement can be performed.

A shown in FIG. 3, the coupling flange 125 couples the crucible holding member 122 to the operation shaft 131 of the crucible forward/backward rotary driving unit 130 to satisfy a predetermined positional relationship as will be described later. The flange 125 consists of heat-resistant nonconductive ceramic. A suitable example of this nonconductive ceramic is "MACOR" (registered trademark) available from Cornings Glass Works. Therefore, the flange 125 is not induction-heated even in a magnetic field generated by the high-frequency induction heating furnace 110. Therefore, the flange 25 does not thermally, adversely affect the unit 130.

FIGS. 8 and 9 are views showing the shape of the crucible 121. FIG. 10 is a sectional view taken along a line 10—10 in FIG. 9.

The crucible 121 is used to heat/melt a dental casting material and to inject the molten material into a mold. Therefore, the crucible 121 has a molten material injection port 121b in a part of an open end of a cup-like crucible main body 121a. The port 121b of the crucible 121 has a sectional shape as shown in FIG. 10. That is, the vertical section of the port 121b is arcuated so that the molten material stayed in the port 121b is separately flowed inside and outside the crucible while the crucible 121 is horizontally held. The crucible 121 preferably consists of platinum containing, e.g., 0.16% of zirconium as an oxide so as not to deform even if it is repeatedly exposed to an environment in which a temperature rapidly rises or falls.

Referring back to FIG. 3, the crucible forward/backward rotary driving unit 130 comprises the operation shaft 131 having the distal end coupled to the coupling flange 125, a shaft guide 132 for guiding the shaft 131, another guide 133, a straight-moving collar 134, a driving force transmitting portion 135, and a crucible-moving motor 136.

The flange 125 and the shaft 131 are coupled to satisfy a predetermined positional relationship so as to position the distal end of the molten material injection port 121b of the crucible 121 on a virtual extended line of the axis of the shaft 131. Therefore, when the crucible is tilted to inject a molten material, almost no variation is produced in distal end position of the port 121b. Therefore, the molten metal can be accurately injected with respect to a mold center.

A groove as indicated by a broken line is formed inside the shaft guide 132. A pin (not shown) extending from the shaft 131 engages with the groove. As shown in FIG. 3, an inclined groove 133a is formed in the guide 133 coupled to the right end of the shaft 131. A pin projecting from the inner surface of the straight-moving collar engages with the groove 133a.

The driving force transmitting portion 135 converts a rotational force of the crucible-moving motor 136 into a linear driving force via a cam 137, a crank 138 and a ball bush 139 and transmits the converted force to the straight-moving collar 134.

Therefore, when the motor 136 rotates to move the collar 134 straight, this linear driving force is transmitted to the operation shaft 131. During transmission of this linear driving force, the shaft 131 is allowed to be rotated due to the relationship between the pin of the collar 134 and the inclined groove 133a. As the pin of the shaft 131 is guided by the groove of the guide 132, the shaft 131 is moved forward/backward and rotated. As a result, the crucible 121 can be inserted/removed with respect to the heating furnace 110 to heat/melt the material, and the molten material can be injected in the mold.

Figure 11:
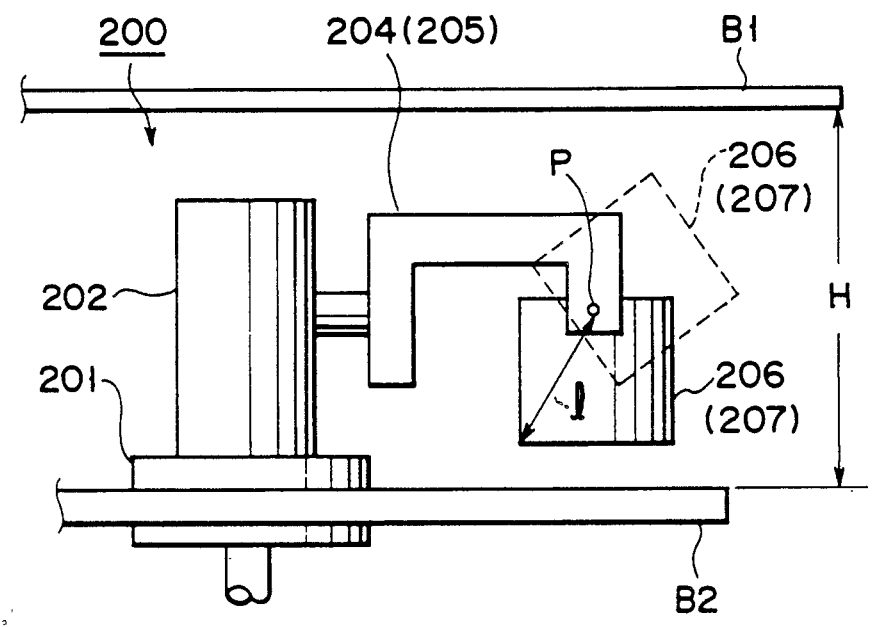

FIG. 11 is a view showing a mounting state of bucket 206 (207) with respect to a bucket holder 204 (205) and a positional relationship between the bucket 206 (207) and the base plates B1 and B2 which partition the box member of the casting apparatus main body 30.

When the centrifugal casting section 200 starts rapid rotation about the rotary shaft 202, the bucket 206 (207) is pivoted upward about a support axis P of the bucket 206 (207). In this case, the bucket 206 (207) must be protected from being collided against the lower surface of the first base plate B1 supporting the casting material melting section or the upper surface of the second base plate B2 supporting the centrifugal casting section 200. Therefore, the dimensions of the bucket is considered as follows. That is, assuming that a distance from the support shaft of the bucket 206 (207) to the circumferential edge of a bottom portion of the bucket 206 (207) located at the farthest position is l and a distance between the first and second base plates B1 and B2 is H, a relation $$H > 2l \tag{1}$$

is satisfied, and the support axis P of the bucket 206 (207) lies midway between the plates B1 and B2. In this manner, the bucket 206 (207) can be protected from collision against the plate B1 or B2.

Figure 12:
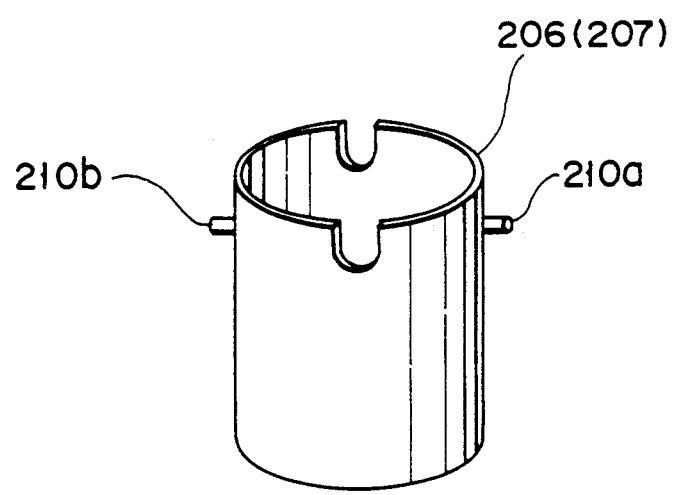

FIG. 12 is a perspective view showing an outer appearance of the bucket 206 (207) described above. As shown in FIG. 12, projecting portions 210a and 210b to be inserted in support holes of the bucket holder 204 (205) extend from the outer circumferential surface near the open end of the bucket 206 (207). A line connecting the portions 210a and 210b is a pivot axis of the bucket 206 (207).

FIGS. 13 and 14 are views showing a detailed structure of a mold to be held in the bucket 206 (207), in which FIG. 13 is a perspective view and FIG. 14 is a sectional view taken along a line 14—14 of FIG. 13. A mold 211 consists of, e.g., an orthophosphate-based investment. A molten material receiving portion 212 for receiving an injected molten material is formed in the center of the upper surface of the mold 211. A cavity 213 having the same shape as a product to be cast such as a crown is formed below the portion 212. The portion 212 is substantially formed into an inverted conical trapezoid as a whole, and its bottom portion 214 is substantially semispherical.

FIG. 15 is a perspective view schematically showing a portion from the bottom portion 214 in order to clarify the shape of the bottom portion 214. It was experimentally confirmed that when the inverted conical trapezoidal molten material receiving portion 212 with the bottom portion 214 having the shape as shown in FIG. 15 was formed, a molten material injected in the mold 211 was not overflown outside the mold 211 even if a shock was applied on the mold 211 upon start of rotation of the centrifugal casting section 200. It was confirmed that a funnel-shaped bottom portion 215 as shown in FIG. 16 could be used instead of the semispherical bottom portion 214 as shown in FIG. 15 to achieve the same effect.

FIGS. 17 and 18 are perspective views showing an arrangement of the casting preheating furnace 401 in the casting preheating section 400 shown in FIG. 2. The mold-preheating furnace 401 is obtained by forming a strainless steel cylindrical member 410 with a bottom as shown in FIG. 17 and winding a sheath heater 411 on the outer circumferential surface and the bottom surface of the cylindrical member 410 as shown in FIG. 18. In an actual operation, the sheath heater 411 is covered with a heat-insulating member.

Figure 19:
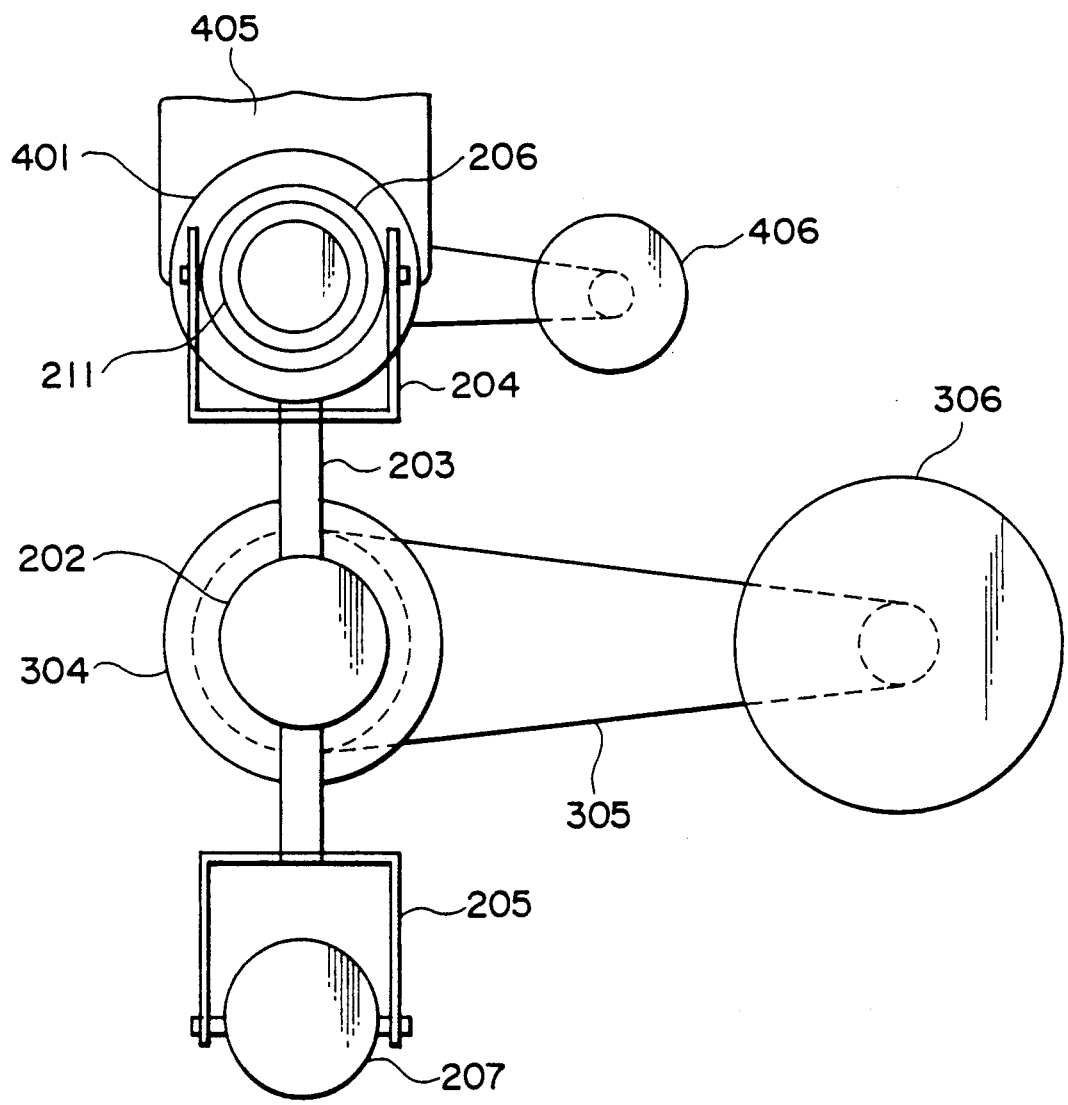

FIG. 19 shows a positional relationship between the centrifugal casting section 200, a part of the rotary driving section 300, and a part of the mold preheating section 400. Referring to FIG. 19, reference numeral 306 denotes a centrifuge-driving motor, and a belt 305 is looped between a rotary shaft of the motor 306 and a pulley 304 coupled to the rotary shaft 202 of the centrifugal casting section 200.

In order to preheat the mold 211 in the mold-preheating furnace 401, a preheating furnace-elevating motor 406 is rotated to move a mold support member 405 upward. As a result, the bucket 206 is received in the mold-preheating furnace 401, and the mold 211 is heated together with the bucket 206. In order to rotate the centrifugal casting section 200 after a molten metal is injected into the mold 211, the motor 406 is rotated in a reverse direction to move the support member 405 downward. As a result, the preheating furnace is removed from the bucket 206.

Figure 20A:
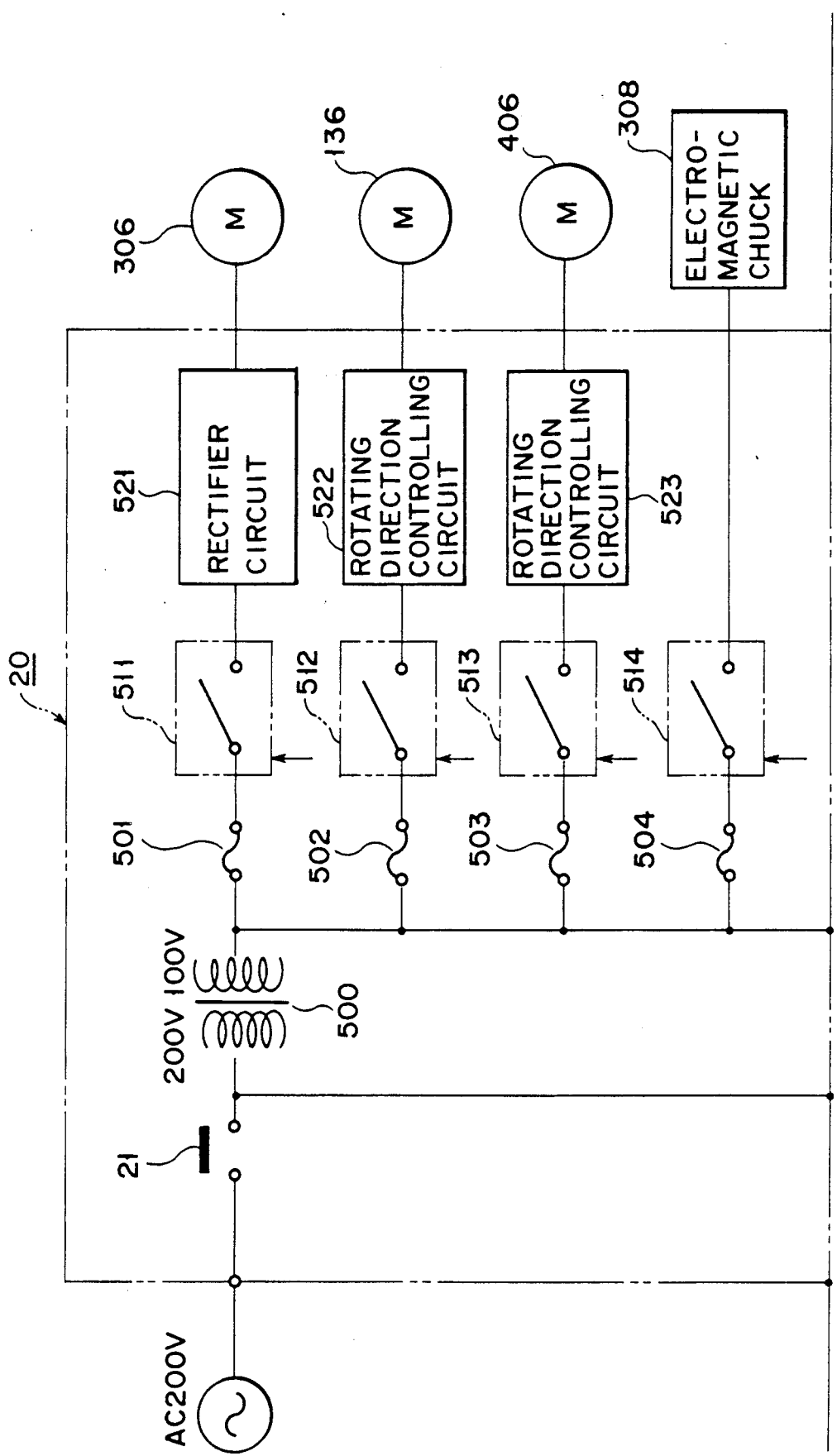
FIGS. 20A and 20B are block diagrams showing an arrangement of an electric system.
Figure 20B:
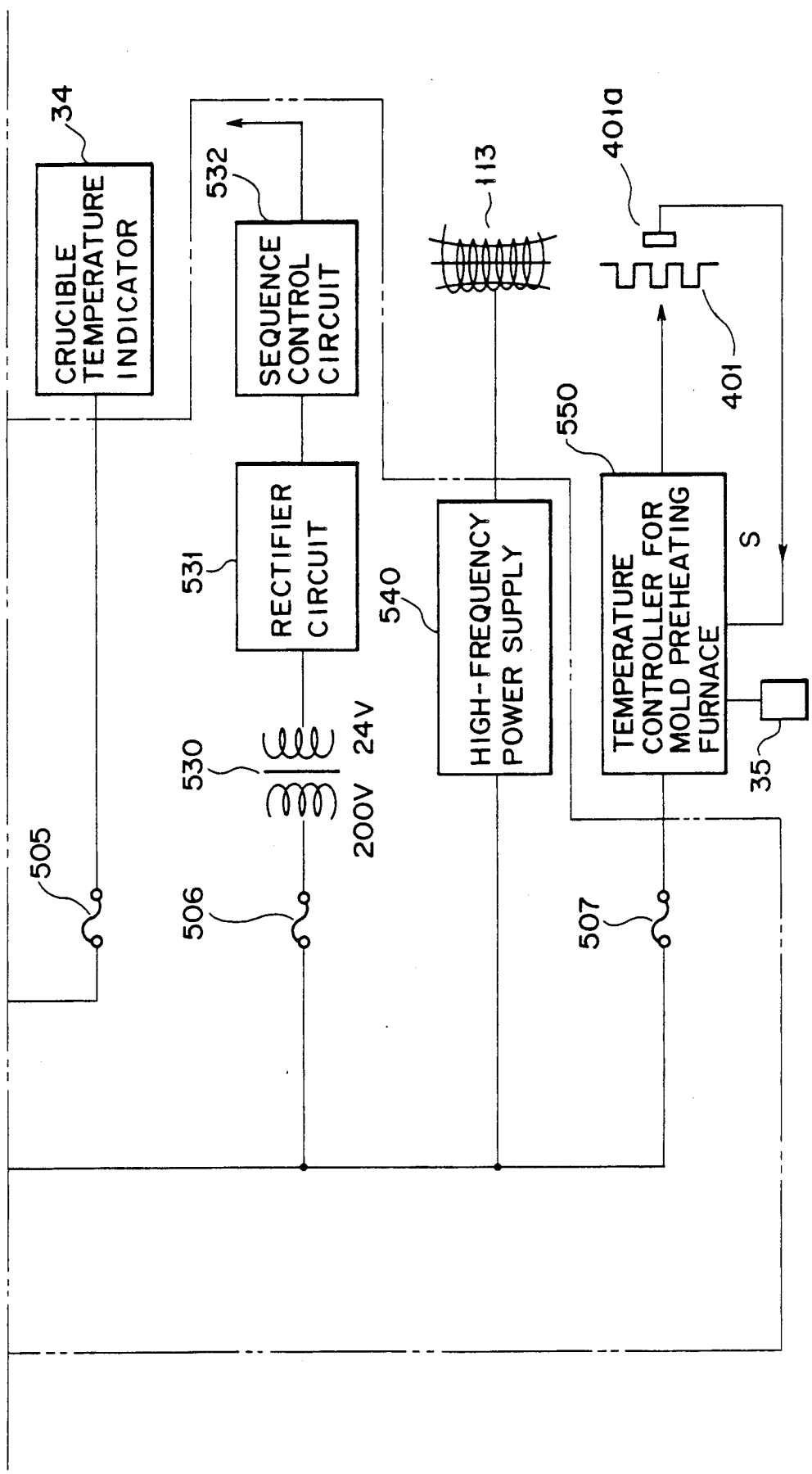

FIGS. 20A and 20B are block diagrams showing an arrangement of an electric system.

The power supply/control unit 20 receives power of AC 200 V. This power is supplied to the respective portions in the unit 20 via the main switch 21. The power transformed from 200 V to 100 V by a transformer 500 is supplied to a rectifier circuit 521 via a fuse 501 and a make contact of a relay 511. A rectified output from the circuit 521 is supplied to the centrifuge-driving motor 306.

The transformed 100-V power is also supplied to a rotating direction-controlling circuit 522 via a fuse 502 and a make contact of a relay 512. Similarly, the above 100-V power is supplied to a rotating direction-controlling circuit 523 via a fuse 503 and a make contact of a relay 523. An output from the circuit 522 is supplied to the crucible-moving motor 136, and an output from the circuit 523 is supplied to the mold-preheating furnace-elevating motor 406.

The 100-V power transformed by the transformer 500 is also supplied to the electromagnetic chuck 308 in the casting apparatus main body 30 via a fuse 504 and a make contact of a relay 514. In addition, this power is supplied to the crucible temperature indicator 34 in the main body 30 via a fuse 505.

The 200-V power supplied from the main switch 21 via a fuse 506 is transformed to 24-V power by the transformer 530 and rectified by a rectifier circuit 531. A rectified output from the circuit 531 is supplied to a sequence control circuit 532. The circuit 532 ON/OFF-controls the relays 511 to 514 at predetermined timings. A high-frequency power supply 540 obtains a high-frequency current of about 27 kHz and several tens to several hundreds ampere from the 200-V power supplied from the main switch 21 and supplies the current to the work coil 113 of the high-frequency induction heating furnace 110.

The 200-V power from the main switch 21 is also supplied to a temperature controller 550 for the mold-preheating furnace via a fuse 507. The controller 550 receives a temperature information signal S concerning mold preheating from a thermocouple 401a provided in the mold-preheating furnace 401 and performs temperature control for the furnace 401 on the basis of the signal S. The temperature of the furnace 401 is indicated by the temperature indicator 35.

A series of operations of the casting apparatus according to the present invention will be described below with reference to a timing chart in FIG. 21.

(1) Water is supplied from the cooling unit to the casting apparatus main body 30, and the main switch 21 of the power supply/control unit 20 is turned on. The upper cover 38 of the main body 30 is opened, and a predetermined amount of a glass material as a dental casting material is put in the platinum crucible 121. The form of this glass material may be any of a rod, a pellet and a powder.

(2) The mold 211 is housed in the bucket 206 held by the bucket holder 204. In order to obtain a good balance, an aluminum cylinder or the like having substantially the same weight as the total weight of the mold 211 and the glass material is housed in the other bucket 207.

(3) The rotary shaft 202 of the centrifugal casting section 200 is manually pivoted to move the mold 211 in the bucket 206 to a predetermined position, i.e., a position in the casting material melting section 100 to receive a molten material dropped from the crucible 121. When the mold 211 is moved to this position, the slits formed in the slit plate 302 are detected by the photosensor 303, and an LED (not shown) is flashed. Therefore, the arrival of the mold 211 to the predetermined position can be checked.

(4) While the LED is flashing, an electromagnetic chuck biasing switch (not shown) is turned on. As a result, the electromagnetic chuck 308 is activated to fix a rotational position of the centrifugal rotary shaft 202. At this time, the LED is set in a continuous ON state.

(5) The upper cover 38 of the main body 30 is closed, and the start button 31 is depressed. As a result, all of heating/melting of the glass material by the casting material melting section 100, injection of the molten glass into the mold 211, casting of the molten glass by the centrifugal casting section 200 and the like are automatically performed as will be described in detail below.

(6) That is, as shown in FIG. 21, when the start button 31 is depressed at time 0, the crucible-moving motor 136 rotates in a normal direction to move the operation shaft 131 straight. Therefore, the crucible 121 is inserted in the high-frequency induction heating furnace 110. In this case, positioning of the crucible 121 is accurately controlled by a photosensor or the like (not shown). At the same time the crucible 121 is inserted in the heating furnace 110, a high-frequency induced current is supplied to the work coil 113. As a result, heating of the crucible 121 is started, and the crucible temperature rises to start melting of the casting material in the crucible 121.

At the same time the start button 131 is depressed, preheating furnace-elevating motor 406 rotates in a normal direction, and the mold-preheating furnace 401 is moved upward by the support member 405. The preheating furnace 401 rises and stops at a position to cover the bucket 206. This positioning is also accurately controlled by a photosensor or the like (not shown). Immediately after positioning, the preheating furnace 401 is powered. As a result, the mold 211 is heated together with the bucket 206 to start preheating. Therefore, the mold-preheating temperature rises.

(7) The high-frequency induced current is maintained constant for about first six minutes and then maintained at a lower value than the above value for the next four minutes. Therefore, the temperature of the crucible 121 rises to 1,450° C. six minutes after activation and then falls to 1,250° C. ten minutes after activation.

The mold-preheating furnace 401 is set to reach a temperature of 600° C. in about first six minutes. Therefore, the glass material is melted about ten minutes after the start button 31 is depressed, and the mold 211 in the bucket 206 is maintained at substantially 600° C.

(8) When 10 minutes has elapsed after the start button 31 is depressed, the high-frequency induced current is cut off. At the same time (or immediately before) the current is cut off, the crucible 121 containing the molten glass is extracted from the high-frequency induction heating furnace 110 and tilted by about 90° to 150° at a predetermined position, and the molten glass in the crucible 12 is naturally dropped accordingly. As shown in FIG. 2, the hole 150 is formed in the base plate B1. Therefore, the molten material naturally dropped as described above is injected in the mold 211 in the bucket 206 set immediately below the hole 150 through the hole 150. The crucible 121 is returned to a horizontal state about two seconds after injection.

(9) At the same time the crucible 121 is returned to the horizontal state, the mold-preheating furnace 401 moves downward from the position to heat the bucket 206 to a position below the second base plate B2. At the same time the furnace 401 falls to the predetermined position, the centrifuge-driving motor 306 is released from a locked state by the electromagnetic chuck 308 and rotates for a predetermined time T1 (about one minute). By a centrifugal force generated upon rotation, the molten glass as a casting material is sufficiently cast in the mold 211. Thereafter, a chime is sounded, and one sequence of operations is finished.

According to the first embodiment as described above, since the coupling flange 125 is formed of a heat-resistant nonconductive ceramic, it is not induction-heated by the work coil 113 even if it is located near the high-frequency induction heating furnace 110. Therefore, the crucible forward/backward rotary driving unit 130 and the like are not adversely affected.

In addition, since the heat-insulating cylindrical member 111, the heat-insulating plate 112, and the crucible holding member 122 constituting the high-frequency induction heating furnace 110 are made of an alumina fiber board, these members have a high heat resistance and a high heat shock resistance. Therefore, even if a temperature is rapidly and repeatedly increased and decreased by induction heating, neither crack nor damage are produced. Therefore, a service life of the high-frequency induction heating furnace 110 can be prolonged, and the material melting crucible 121 can be stably held for a long time period.

Furthermore, the platinum crucible is used as the material melting crucible 121, the scald contact side of the platinum-based thermocouple 127 for temperature measurement is connected to the outer surface of the crucible 121 by means of, e.g., scalding at a comparatively low temperature, and the other end portion of the thermocouple 127 is fixed to the flange 125 of the crucible holding member 122 for holding the crucible 121 by machine screws and then externally extracted by the extension lead wire 129 of the thermocouple. Therefore, temperature measurement can be accurately performed following only changes in crucible heating temperature without being adversely affected by induction heating. In addition, the thermocouple 127 is not twisted upon rotation of the crucible holding unit 120.

(2nd Embodiment)

The second embodiment of the present invention will be described below with reference to FIGS. 22 to 29. The second embodiment is the same as the above first embodiment except that the mold-preheating furnace 401 and the arm positioning electromagnetic chuck 308 are omitted and a detachable crucible holding unit and an improved crucible forward/backward rotary driving unit are additionally used.

Figure 22:
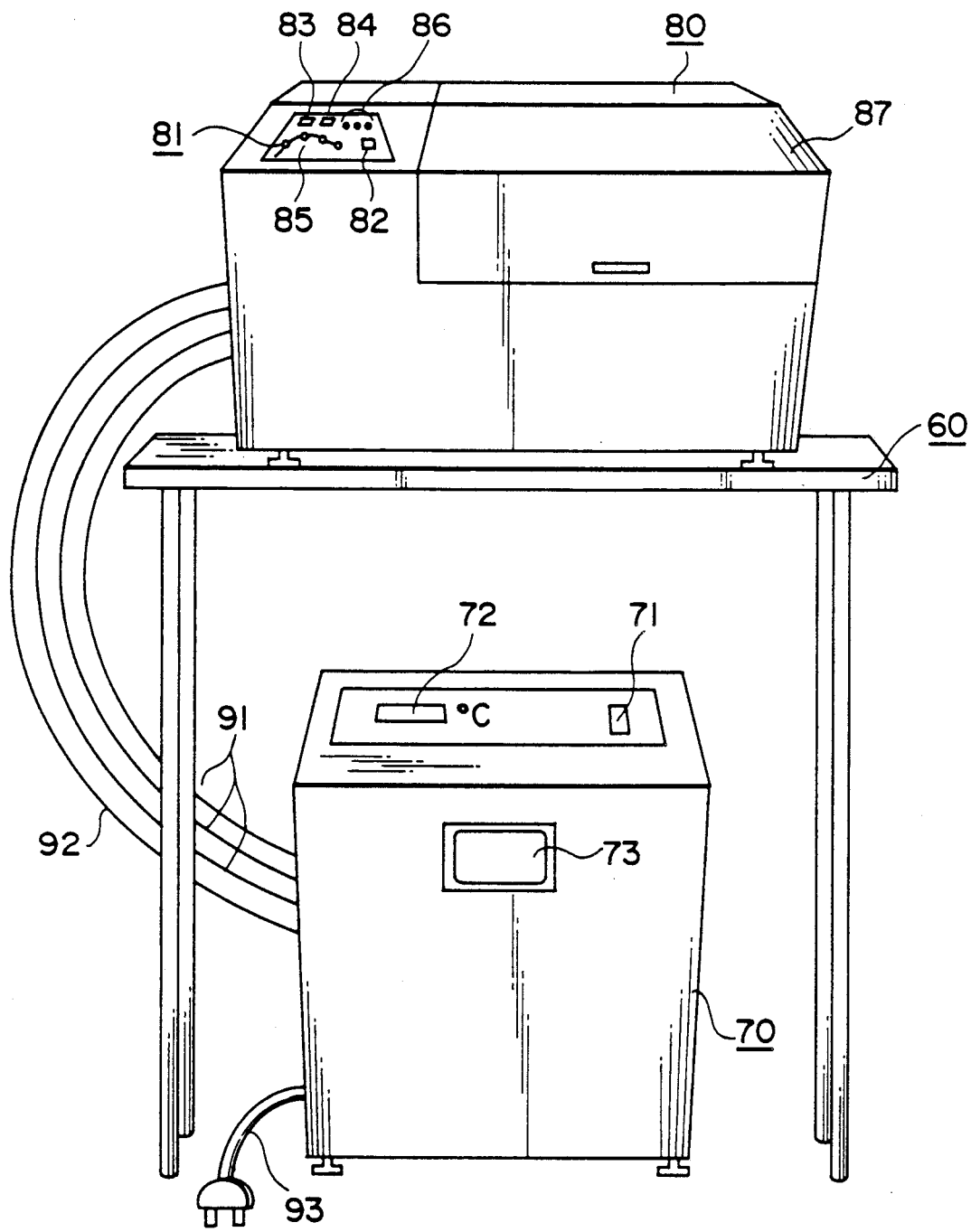

FIG. 22 is a front view showing an installation state of a dental centrifugal casting apparatus according to the second embodiment of the present invention. A power supply unit 70 is placed below a casting apparatus installation table 60, and a casting apparatus main body 80 is placed on the table 60. That is, this apparatus is of a separation type, and the two separate parts are connected by cables 91 such as a signal line cable, an extension lead wire cable for a platinum thermocouple and a motor driving cable, and a high-frequency power supply feeder 92 for supplying high-frequency power to a work coil of a high-frequency induction heating furnace. A commercial AC power supply cable 93 with a plug is connected to the power supply unit 70.

A main switch 71 and a crucible current temperature indicator 72 are mounted on a case upper surface of the unit 70. A temperature adjuster 73 also serving as a temperature indicator for program-controlling a crucible temperature is provided in the unit 70 so that its indication surface is exposed on the case front surface. Although not shown, the unit 70 also houses a high-frequency power supply unit using an inverter circuit, a capacitor for forming a series oscillation circuit with the work coil, a matching transformer for obtaining impedance matching, and a sequence control circuit for controlling the overall apparatus to perform a sequence operation.

Although not shown, the casting apparatus main body 80 has a water supply/drainage port for supplying/draining work coil cooling water at a case rear surface side. The water supply/drainage port can be arbitrarily connected to a water plug by a flexible hoses.

An operation panel 81 is provided at the left side of the upper surface of the casting apparatus main body 80. The panel 81 includes a "start/cast" button 82 having a first function of starting the sequence operation and a second function of injecting a molten casting material (glass) into a mold and applying a centrifugal force to perform casting, a "stop" button 83 for interrupting all operations in an emergency, and a "reset" button 84 for moving a crucible to an initial position. The operation panel 81 also includes a temperature pattern indication lamp 85 and an abnormality indication lamp 86. The temperature pattern indication lamp 85 indicates a temperature pattern of the crucible. The abnormality indication lamp 86 indicates abnormality when an abnormal excess current flows through the power supply unit 70 or the crucible temperature is much higher or lower than a programmed temperature.

A cove 87 is provided at the right side of the case upper surface of the main body 80 so as to be freely opened/closed. The cover 87 is open when a dental casting material such as glass is set in the crucible, a mold preheated outside is set in a bucket, or the mold after casting is extracted outside FIG. 23 is a side view showing the interior of the casting apparatus main body 80, and FIG. 24 is a plan view showing the interior of the main body 80.

Figure 23:
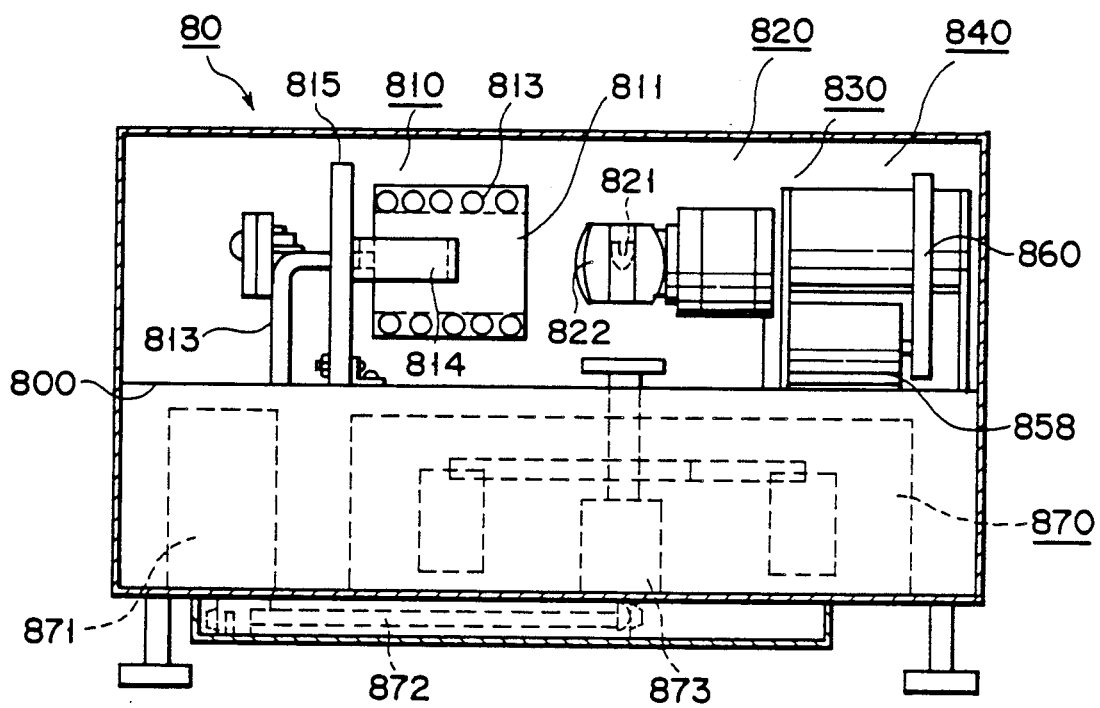
Figure 24:
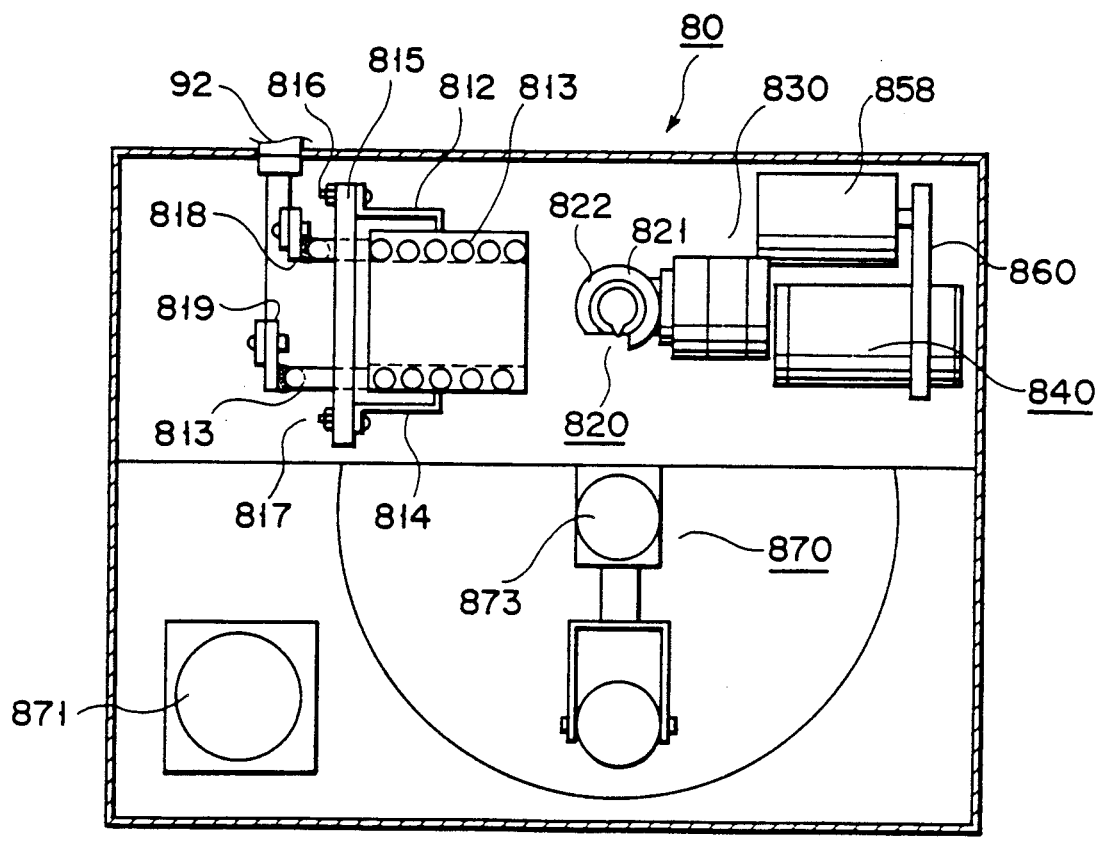

As shown in FIGS. 23 and 24, a high-frequency induction heating furnace 810 including a furnace member 811 (constituted by a heat-insulating cylinder and a heat-insulating plate as in the first embodiment) is located above a partition 800 of the main body 80, and about ten turns of a work coil 813 consisting of a copper pipe having an outer diameter of $\phi$ 5 to 6 and an inner diameter of $\phi$ 3 to 4 and covered with an insulating coating are wound around the outer circumferential surface of the furnace member 811. The work coil 813 has an inner diameter of $\phi 60$ and a length of 60 mm. Right and left central portions of the coil 813 are brazed with silver to the distal ends of L-shaped support metal pieces 812 and 814. The proximal ends of the metal pieces 812 and 814 are fixed to a holding plate 815 consisting of a ceramic material having a high heat resistance by bolts 816 and 817. Both the end portions of the coil 813 are extracted to the rear side through the holding plate 815. Both the extracted extended end portions of the coil 813 are bent downward at a right angle and connected to the water supply/drainage port (not shown) via a hose having a high insulation property. Although not shown, a check valve is mounted on a water supply path of the two extended end portions of the coil 813, and a flow meter for measuring a flow rate of a cooling water is mounted on a drainage path. Terminals 818 and 819 are brazed with silver to the two extended end portions of the coil 813 extracted to the rear side through the holding plate 815. The end portion of the feeder 92 is connected to the terminal 818 and 819 by machine screws.

A crucible holding unit 820, an attaching/detaching means 830, a crucible forward/backward rotary driving unit 840 and the like are arranged in a position opposing the heating furnace 810 located on the partition 800. As will be described in detail later, reference numeral 821 denotes a crucible; 822, a crucible holding member; 858, a driving motor; and 860, a timing belt.

A centrifuge unit 870 is placed below the partition 800 of the casting apparatus main body 80. In the unit 870, a rotational force of a centrifuge-driving motor 871 is transmitted to a rotary main shaft 873 by a belt 872, and a centrifugal force is applied to a mold and a molten material by rotation of the shaft 873, thereby performing casting.

Figure 25:
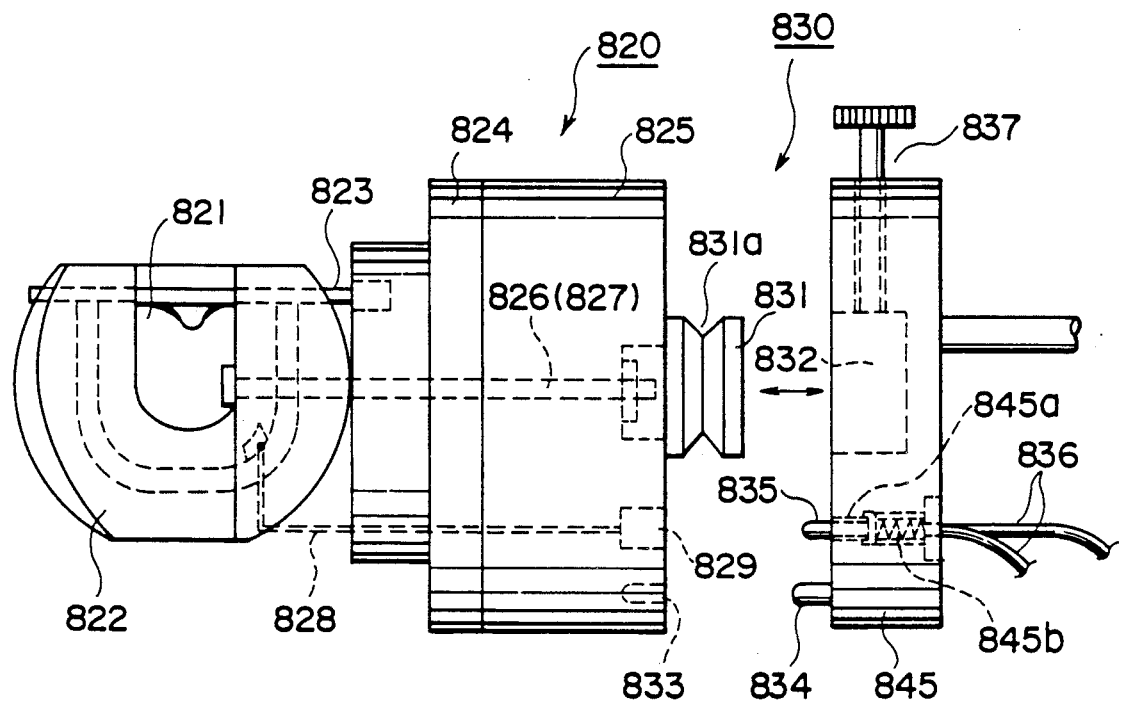
Figure 26:
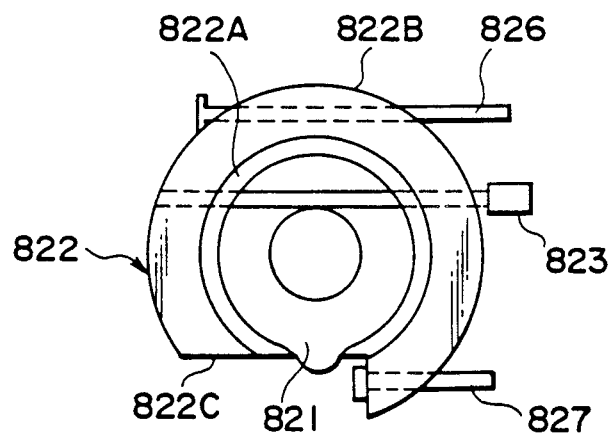

FIG. 25 is a side view of the crucible holding unit 820, and FIG. 26 is a plan view showing only the crucible 821 in the unit 820.

As shown in FIG. 25, in the crucible holding unit 820, the platinum crucible 821 is held by a crucible holding member 822, and a coupling flange 825 is provided for the member 822 via a heat-insulating plate 824 consisting of a heat-insulating material. The unit 820 is detachably connected to a coupling flange 845 of the crucible forward/backward rotary driving unit 840 (to be described latter) via the attaching/detaching means 830.

Reference numeral 823 denotes a crucible urging pin made of platinum; 826 and 827, crucible holding member mounting machine screws made of alumina; 828, a platinum-based thermocouple; and 829, a terminal of the thermocouple. Although only one terminal 829 is shown in FIG. 25, the terminal 829 is actually a pair of columnar terminals connected to the two end portions of the thermocouple 828. The terminals 829 are embedded with a predetermined interval therebetween in an eccentric position of the right end face (in FIG. 25) of the flange 825 so that one end face of each terminal is exposed on the flange surface.

As shown in FIG. 26, the crucible holding member 822 is constituted by a member 822A which consists of, e.g., an alumina fiber having high heat-insulating properties, heat resistance and heat shock resistance and holds the platinum crucible 821, and a member 822B which consists of, e.g., aluminum titanate having high physical strength, heat resistance and heat shock resistance and holds the member 822A. A notched portion 822C is formed to smoothly perform a molten material injection operation and has the same meaning as that of the notched portion 122a in the first embodiment. Note that the notched portion 822C is formed by cutting the left half of the crucible holding member 822 as shown in FIG. 26. Since the notched portion 822C is formed in this manner, a part of the crucible holding member 822 does not interfere with a tightening operation of the machine screws 827 or the like. Therefore, the tightening operation of the machine screws 827 or the like can be smoothly performed. In addition, the above shape can be easily manufactured.

The attaching/detaching means 830 has the following arrangement. A first engaging portion 831 consisting of a pulley-like columnar projecting portion is formed at the central portion of the right end face (in FIG. 25) of the coupling flange 825 provided for the crucible holding member 822. A second engaging portion 832 consisting of a cylindrical recess portion to be engaged with the first engaging portion 831 is formed at the central portion of the left end face (FIG. 25) of the coupling flange 845 provided at the distal end of the crucible forward/backward rotary driving unit 840. By engaging the first and second engaging portions 831 and 832, the unit 820 can be detachably connected to the unit 840.

A hole 833 is formed in a position far from the central position of the right end face (FIG. 25) of the flange 825 of the crucible holding unit 820. A projection 834 to be fitted in the hole 833 is formed in a position far from the central position of the left end face (FIG. 25) of the flange 845 of the crucible forward/backward rotary driving unit 840. By fitting the projection 834 in the hole 833, positioning in the rotational direction of the units 820 and 840 is performed. A pair of pin terminals 835 (although only one terminal is shown in FIG. 25) are formed in a position opposing the pair of embedded terminals 829 in the left end face (FIG. 25) of the flange 845. Each terminal 835 is inserted in a corresponding one of a pair of terminal holding holes 845a so as to project from the surface of the flange 845 or to be pushed below the surface within a predetermined depth range. A pair of coil springs 845b is placed in a compression state between the proximal end portion of each pin terminal 835 and the bottom portion of a corresponding one of the hole 845a. Each terminal 835 is normally biased by the each of spring 845b to project from the surface of the flange 845 by a predetermined length.

When the flanges 825 and 845 engage with each other, the distal end portion of each terminal 835 is pressed by the exposed surface of a corresponding one of the pair of embedded terminals 829 and pushed inside the each hole 845a. The terminals 835 are pushed while compressing the coil springs 845b. Therefore, the distal end portion of the pin terminals 835 and the exposed surface of the embedded terminals 829 are brought into contact with each other by a high pressure. As a result, the pair of terminals 829 and the pair of terminals 835 are electrically connected to each other. The pin terminals 835 are connected to end portions of a pair of extension lead wires 836 guided from the rear surface side of the coupling flange 845.

A locking means is provided between the first and second engaging portions 831 and 832 to prevent the first engaging portion 831 from being disengaged from the second engaging portion 832. This locking means is constituted by a V-shaped annular groove 831a formed in the outer circumferential surface of the first engaging portion 831 consisting of the columnar projecting portion at the flange 825 side, and a locking screw 837 having a distal end portion facing the inner circumferential surface of the second engaging portion 832 consisting of the cylindrical recess portion at the flange 845 side. The screw 837 is threadably engaged with the flange 845 so a to be freely inserted in/removed from the flange 845. That is, the distal end of the screw 837 of the locking means is inserted in the groove 831a of the first engaging portion 831 engaged with the second engaging portion 832 to prevent the first engaging portion 831 from being disengaged from the second engaging portion 832.

Note that a platinum alloy-based crucible which can be repeatedly used is used as the crucible 821 and prepared for each crucible holding unit 820.

In this manner, the entire crucible holding unit 820 can be arbitrarily attached to/detached from the crucible forward/backward rotary driving unit 840 while the crucible 821 is held. Therefore, when the crucible 821 must be replaced with another to perform casting in order to use a casting material of another type, the locking screw 837 is loosened to remove the currently used crucible holding unit 820 from the driving unit 840. Thereafter, another crucible holding unit 820 holding a predetermined crucible prepared beforehand is mounted on the driving unit 840 by tightening the screw 837. That is, the first engaging portion 831 is engaged with the second engaging portion 832, and the screw 837 is tightened. As a result, the distal end of the screw 837 is inserted in the V-shaped groove formed in the outer circumferential surface of the columnar projecting portion. Therefore, removal of the first engaging portion 831 can be prevented.

Since the crucible holding unit 820 can be simply attached/detached to/from the crucible forward/backward rotary driving unit 840, a material having a different glass composition or glass having a different content of a coloring agent can be used as a casting material by simply replacing the unit 820. Therefore, working efficiency of a dental technician can be increased.

Note that an operation may be simplified by using, instead of the locking screw 837, a locking pin mechanism (not shown) comprising a locking pin and a coil spring for constantly biasing the locking pin to displace it in an axial direction.

FIGS. 27 and 28 are exploded perspective views showing an arrangement of the crucible forward/backward rotary driving unit 840.

Referring to FIG. 27, reference numeral 841 denotes a columnar operation shaft. The coupling flange 845 is fitted on and fixed to one end of the shaft 841. A pin screw hole 842 is formed in the outer circumferential surface close to the other end of the shaft 841. A guide pin 843 is threadably engaged with the hole 842 via a groove formed in the circumferential wall of a guide cylinder and a driving cylinder (to be described later). In order to reduce a sliding friction between the guide pin 843 and the groove, a pair of rollers 844a and 844b and a spacer 844c are fitted on the pin 843.

The guide cylinder 846 has a shaft hole 847 for slidably and pivotally holding the operation shaft 841 along its axis. A first guide groove 848a for guiding the pin 843 in a direction parallel to the axis of the cylinder 846 and a second guide groove 848b continuous with the first guide groove 848a, for guiding the pin 843 about the axis of the cylinder 846 are formed in the circumferential wall of the cylinder 846. The two ends of the guide cylinder 846 are sandwiched between support plates 849 and 850. The two end faces of the guide cylinder 846 and the plates 849 and 850 are fixed by a plurality of machine screws 851 to 854.

A driving cylinder 855 is rotatably fitted on the outer circumferential surface of the guide cylinder 846. A spiral groove 856 to be engaged with the guide pin 843 is formed in the circumferential wall of the driving cylinder 855. A gear portion 857 is formed on the outer circumferential surface at one end of the cylinder 855.

FIG. 28 is a perspective view showing a coupling relationship between the driving cylinder 855 and driving control system located near one end of the cylinder 855. The driving control system has the following arrangement. That is, a timing belt 860 is looped between a driving gear 859 mounted on a shaft of a driving motor 858 rotatable in both normal and reverse directions and the gear portion 857 of the driving cylinder 855. An arcuated index piece 864 is mounted on one end face of the cylinder 855. The index piece 864 can pass through gap portions formed in three photointerrupters 861, 862 and 863. The photointerrupters 861, 862 and 863 sense passing of the index piece 864, thereby sensing a pivoting angle of the driving cylinder 855. The driving motor 858 is controlled on the basis of information obtained by this sensing, thereby positioning the operation shaft 841.

When the driving motor 858 is rotated in a normal direction, this rotational force is transmitted to the driving cylinder 855 by the timing belt 860. Therefore, the cylinder 855 is rotated in a normal direction indicated by an arrow in FIG. 27. Therefore, the spiral groove 856 applies a moving force toward the upper left side in FIG. 27 to the guide pin 843. The movement of the pin 843 is limited such that the pin 843 can move only long the guide grooves 848a and 848b of the guide cylinder 846. Therefore, when the moving force is applied, the pin 843 located at a point b circumferentially moves (toward the upper side in FIG. 27) along the second guide groove 848b to a connection point c between the first and second guide grooves 848a and 848b. The pin 843 then moves along the axial direction (toward the left side in FIG. 27) along the first guide groove 848a to a point a.

When the driving motor 858 is rotated in a reverse direction, the above operation is performed in a reverse direction. As a result, the guide pin 843 moves from the point a in the axial direction along the first guide groove 848a to the connection point c. The pin 843 then circumferentially moves along the second guide groove 848b to a point b.

The above movement of the pin 843 directly represents those of the operation shaft 841 and the crucible 821. That is, when the guide pin 843 is located at the point c, the crucible 821 is in its initial position. When the pin 843 moves to the point a, the crucible 821 moves forward to a melting position in the furnace member 811. In this state, when the pin 843 moves to the point b via the point c, the crucible 821 is extracted to a predetermined position outside the furnace member and pivoted through about 120°, thereby injecting a molten material into a mold. Positioning of the above three points a, b and c is performed by the sensing operation by the index piece 864 and the photointerrupters 861 to 863.

Figure 29:
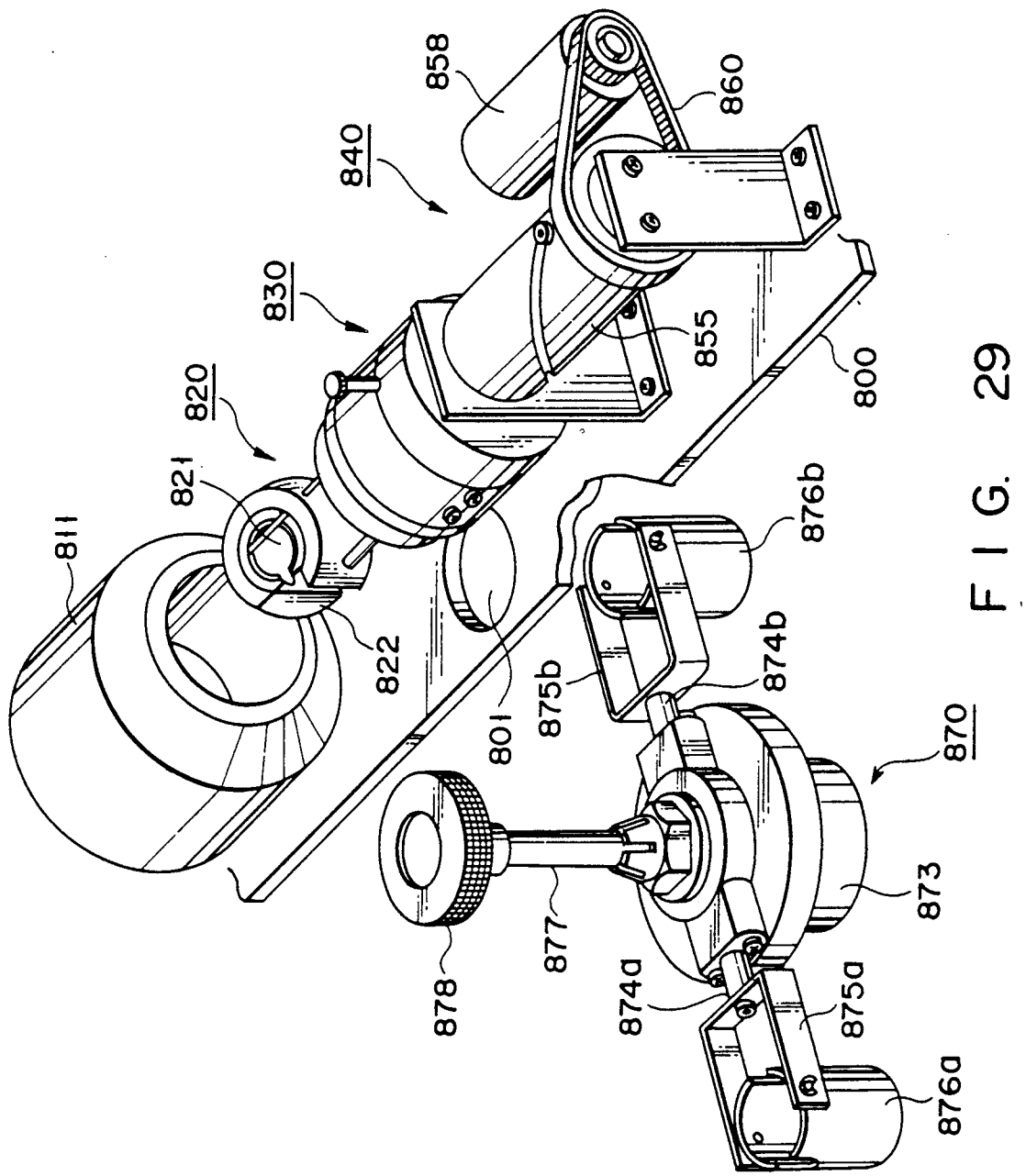

FIG. 29 is a perspective view showing only a main part of the casting apparatus main body 80. As shown in FIG. 29, the centrifuge unit 870 has a pair of arms 874a and 874b perpendicular to the axis of a rotary spindle 873. A mold holding bucket 876a (876b) is swingably mounted on the distal end of the arm 874a (874b) via a bucket holder 875a (875b) consisting of a U-shaped frame. The bucket 876a (876b) has the same structure as shown in FIG. 12. A mold (not shown) is held by the bucket 876a (876b). A knob 878 is connected to the upper end portion of the rotary spindle 873 via a shaft 877.

Upon injection of a molten metal, a molten metal in the crucible 821 is injected into a mold (not shown) held in each bucket positioned by the knob 878 through a through hole 801 formed in the partition 800. Subsequently, the shaft 873 is rotated to rotate the buckets 876a and 876b. As a result, a centrifugal force is applied to the mold and the molten metal in each of the buckets 876a and 876b, thereby casting the molten material.

An overall operation of the second embodiment will be described below. First, cooling water is flowed. The main switch of the power supply unit 70 is turned on. The cover 87 of the casting apparatus main body 80 is opened. A dental casting material such as a glass material is put into the crucible 821. The cover 87 is closed. The "start/cast" button 82 is depressed. As a result, the crucible 821 is inserted in the furnace member 811. The high-frequency power supply is switched on, and a high-frequency current is flowed to the work coil 813 via the feeder 92. The temperature of the platinum crucible 821 rises to 1,450° C. in about 5 to 10 minutes, and the material is melted. Thereafter, when the temperature is decreased to 1,250° C., a buzzer is sounded to alarm that a standby state capable of casting is set.

In order to obtain a predetermined set crucible temperature, the high-frequency current to be supplied to the work coil 813 is program-controlled by the temperature adjuster 73. An actual crucible temperature is measured by the platinum-based thermocouple 828. Information about the measured temperature is fed back to the temperature adjuster 73.

The cover 87 is opened, and a mold preheated up to 600° C. is placed in one of the buckets, e.g., the bucket 876b. An aluminum balancer having the same weight as the mold is placed in the other bucket 876a. The knob 878 is rotated to position the mold immediately below the hole 801 of the partition 800. This positioning is performed by a sensing operation by a sensor (not shown) having the same arrangement as the index piece 864 and the interrupters 861 to 863. The cover 87 is closed. The "start/cast" button 82 is depressed again. As a result, the crucible 821 is extracted from the furnace member 811 and pivoted through 120° above the through hole 801. Therefore, the molten material is injected into the mold. The crucible 821 is returned to the initial state in about two seconds. At the same time, the centrifuge-driving motor 871 is turned on to rotate the rotary spindle 873 at high speed, thereby performing an centrifugal operation for about one minute. The molten material is cast inside the mold by a centrifugal force generated by the centrifugal operation. Thereafter, when the buzzer is sounded, the cover 87 is opened to extract the mold after casting.

According to the above embodiment, a series of processes of, e.g., heating/melting of a material, injection of the material into a mold, and rotation and stop of the centrifuge unit 870 can be substantially automatically performed. Therefore, even an unskilled operator can easily operate the casting apparatus to perform casting.

Since the high-frequency induced heating furnace 810 is used as a heating/melting means, the casting material can be heated/melted with high efficiency, and the apparatus can be made compact.

The apparatus is arranged such that the centrifuge unit 870 rotates at high speed at the same time the heated/melted material is dropped into the mold. Therefore, the casting operation can be finished before cooling/solidification of the casting material progresses.

In addition, the position of the mold changes together with the bucket 876a or 876b in accordance with rotation of the centrifuge unit 870. Therefore, the molten material can be protected from being overflown from the mold due to a shock upon start of rotation of the centrifuge unit or a centrifugal force during a high-speed rotation.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A dental centrifugal casting apparatus comprising:
a crucible for receiving a dental casting material;
a crucible holding unit for holding said crucible;
a heating furnace for heating and melting the dental casting material in said crucible;
a crucible forward and backward rotary driving unit for driving said crucible holding unit forward and backward so as to insert said crucible into said heating furnace to heat and melt the material in said crucible and to remove the crucible from said furnace and for rotationally driving said crucible holding unit so as to inject the melted material into a mold at a predetermined position;
a bucket for holding said mold in which the molten material is injected by the forward and backward motion and the rotation of said crucible performed by said crucible forward and backward rotary driving unit; and
a centrifuge unit for rotating a rotary arm swingably mounting said bucket on an end portion thereof at high speed immediately after the material is injected to apply a centrifugal force to the mold and molten material, thereby performing casting.

2. An apparatus according to claim 1, wherein said heating furnace for heating and melting the dental casting material is a high-frequency induction heating furnace.

3. An apparatus according to claim 1, wherein said crucible for receiving the dental casting material is a platinum-based crucible.

4. An apparatus according to claim 3, wherein a temperature contact portion of a platinum-based thermocouple for temperature measurement is connected and fixed to an outer surface of said platinum-based crucible for receiving the dental casting material, the other end of said thermocouple is fixed to an outer surface of a distal end portion of said crucible holding unit, and the other end portion of said fixed thermocouple is connected to a crucible temperature adjuster by an extension lead wire of said thermocouple.

5. An apparatus according to claim 2, wherein a crucible holding member for holding said crucible comprises an alumina fiber board.

6. An apparatus according to claim 2, wherein a crucible holding member of said crucible holding unit for directly holding said crucible holds an outer surface of said crucible by a member such as an alumina fiber having high heat-insulating properties, heat resistance and heat shock resistance and holds an outer surface of said member by a member such as an aluminum titanate having high physical strength, heat resistance and heat shock resistance.

7. An apparatus according to claim 1, further comprising:
a first engaging portion formed at a proximal end portion of said crucible holding unit; and
a second engaging portion formed at a distal end portion of said crucible forward and backward rotary driving unit for driving forward and backward and rotationally driving said crucible holding unit, said second engaging portion being engaged with said first engaging portion,
wherein said crucible holding unit can be detachably connected to said crucible forward/backward rotary driving unit by engaging said first and second engaging portions.

8. An apparatus according to claim 1, wherein said crucible forward and backward rotary driving unit comprises:
a columnar operation shaft having one end connected to a proximal end portion of said crucible holding unit and a guide pin extending from a outer circumferential surface close to the other end thereof;
a guide cylinder having a shaft hole for slidably and pivotally holding said operation shaft, a first guide groove, formed in a circumferential wall of said guide cylinder, for guiding said guide pin in a direction parallel to an axis, and a second guide groove, formed in the circumferential wall of said guide cylinder to be continuous with said first guide groove, for guiding said guide pin about the axis; and
a driving cylinder, pivotally fitted on an outer circumferential surface of said guide cylinder, having a spiral groove formed in a circumferential surface of said driving cylinder so as to be engaged with said guide pin, and rotated by power supplied from a driving source to move said guide pin along said first and second guide grooves.

9. An apparatus according to claim 1, wherein a molten material injection port of said crucible has an arcuated vertical section so that the molten material separately flows inside and outside said crucible when said crucible is held in a horizontal state.

10. An apparatus according to claim 2, wherein a coupling flange for coupling said crucible holding member for holding said crucible to said operation shaft of said crucible forward and backward rotary driving unit so as to satisfy a predetermined positional relationship consists of a heat-resistant nonconductive ceramic.

11. An apparatus according to claim 2, wherein a heat-insulating cylinder constituting a furnace member of said high-frequency induction heating furnace and a heat-insulating plate for closing an open end of said heat-insulating cylinder comprises an alumina fiber board.

* * * * *